US012766286B2

(12) United States Patent
Kimble et al.

(10) Patent No.: US 12,766,286 B2
(45) Date of Patent: Oct. 20, 2026

(54) HEATER PLATE FOR RESPIRATORY HUMIDIFICATION SYSTEMS

(71) Applicant: Fisher & Paykel Healthcare Limited, Auckland (NZ)

(72) Inventors: Lloyd Dylan Kimble, Auckland (NZ); Weng Ip Tong, Auckland (NZ); Houde Huang, Auckland (NZ); Andrew Chi Lup Lau, Auckland (NZ); Emily Joyce Hargrave-Thomas, Auckland (NZ); Simon John Gray, Auckland (NZ); Timothy James Beresford Sharp, Auckland (NZ); Sean Joel Babbage, Auckland (NZ); Hayk Noobar Antranik Yaghobian, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 418 days.

(21) Appl. No.: 17/660,896

(22) Filed: Apr. 27, 2022

(65) Prior Publication Data

US 2022/0339393 A1 Oct. 27, 2022

Related U.S. Application Data

(63) Continuation of application No. 16/213,290, filed on Dec. 7, 2018, now Pat. No. 11,351,331.

(Continued)

(51) Int. Cl.

*A61M 16/16* (2006.01)
*A61M 16/06* (2006.01)

(Continued)

(52) U.S. Cl.

CPC ........ *A61M 16/16* (2013.01); *A61M 16/0666* (2013.01); *A61M 16/1065* (2014.02);

(Continued)

(58) Field of Classification Search

CPC .............. A61M 16/16; A61M 16/0051; A61M 16/0066; A61M 16/0666; A61M 16/1065;

(Continued)

(56) References Cited

U.S. PATENT DOCUMENTS 3,191,003 A * 6/1965 Yohe .................... F24C 15/105 219/465.1
4,203,027 A * 5/1980 O'Hare ................ A61M 16/16 261/142

(Continued)

FOREIGN PATENT DOCUMENTS

WO WO 2008/056993 A2 5/2008

*Primary Examiner* — Bradley H Philips
(74) *Attorney, Agent, or Firm* — VIA LLP

(57) ABSTRACT

A respiratory humidification system humidifies a flow of respiratory gases supplied to a user. The system can include a main housing that receives a humidification chamber, a heating plate included in the main housing and positioned to contact the humidified chamber and transfer heat to the humidifier chamber, and a heating element that provides heat to the heating plate. The heating element can include a temperature sensor disposed in a central region of the heating element. Disposing the temperature sensor in the central region can reduce a likelihood that conductors of the heating element will cause an incorrect temperature measurement by the temperature sensor.

15 Claims, 30 Drawing Sheets

Related U.S. Application Data

(60) Provisional application No. 62/596,635, filed on Dec. 8, 2017.

(51) Int. Cl.
*A61M 16/10* (2006.01)
*A61M 16/00* (2006.01)
*A61M 16/20* (2006.01)

(52) U.S. Cl.
CPC ... *A61M 16/109* (2014.02); *A61M 2016/0039* (2013.01); *A61M 16/0051* (2013.01); *A61M 16/0066* (2013.01); *A61M 16/1095* (2014.02); *A61M 16/161* (2014.02); *A61M 16/20* (2013.01); *A61M 2205/18* (2013.01); *A61M 2205/3317* (2013.01); *A61M 2205/3334* (2013.01); *A61M 2205/3365* (2013.01); *A61M 2205/3368* (2013.01); *A61M 2205/3375* (2013.01); *A61M 2205/3569* (2013.01); *A61M 2205/3653* (2013.01); *A61M 2205/505* (2013.01); *A61M 2230/205* (2013.01); *A61M 2230/432* (2013.01)

(58) Field of Classification Search
CPC ............ A61M 16/109; A61M 16/1095; A61M 16/161; A61M 16/20; A61M 2016/0039; A61M 2205/18; A61M 2205/3317; A61M 2205/3334; A61M 2205/3365; A61M 2205/3368; A61M 2205/3375; A61M 2205/3569; A61M 2205/3653; A61M 2205/505; H05B 3/20; H05B 3/68; H05B 3/60
See application file for complete search history.

(56) References Cited

U.S. PATENT DOCUMENTS

| | | | | |
|---|---|---|---|---|
| 4,723,067 | A * | 2/1988 | Schreder | F24C 15/105<br>219/512 |
| 4,859,835 | A * | 8/1989 | Balderson | H05B 3/748<br>338/308 |
| 5,522,308 | A * | 6/1996 | Kayashima | G05D 23/2401<br>219/442 |
| 6,046,438 | A * | 4/2000 | Slegt | H05B 3/82<br>219/448.11 |
| 6,924,468 | B2 | 8/2005 | Abbott et al. | |
| 11,351,331 | B2 | 6/2022 | Kimble et al. | |
| 2002/0011480 | A1 * | 1/2002 | Schilling | H05B 3/746<br>219/448.11 |
| 2002/0134775 | A1 * | 9/2002 | Ohashi | H05B 3/143<br>219/465.1 |
| 2004/0026411 | A1 * | 2/2004 | Mucke | A47L 15/4285<br>219/543 |
| 2007/0284361 | A1 * | 12/2007 | Nadjafizadeh | A61M 16/021<br>219/442 |
| 2009/0107980 | A1 * | 4/2009 | Andel | A61M 16/109<br>219/443.1 |
| 2009/0107982 | A1 | 4/2009 | McGhin et al. | |
| 2010/0147299 | A1 | 6/2010 | Row et al. | |
| 2012/0097163 | A1 | 4/2012 | Potharaju et al. | |
| 2013/0248509 | A1 * | 9/2013 | Unno | H01L 21/67103<br>219/521 |
| 2014/0131904 | A1 * | 5/2014 | Tang | A61M 16/022<br>261/157 |
| 2014/0216459 | A1 | 8/2014 | Vos et al. | |
| 2015/0048530 | A1 * | 2/2015 | Cheung | A61M 16/024<br>261/135 |
| 2016/0354573 | A1 | 12/2016 | Buswell et al. | |
| 2017/0059190 | A1 * | 3/2017 | Stefanski | G05D 23/193 |
| 2018/0193185 | A1 * | 7/2018 | Thomas | A61F 7/007 |

* cited by examiner

HEATER PLATE FOR RESPIRATORY HUMIDIFICATION SYSTEMS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. Specifically, this application is a continuation of U.S. patent application Ser. No. 16/213,290, filed Dec. 7, 2018, now U.S. Pat. No. 11,351,331, which claims the priority benefit of U.S. Provisional Application No. 62/596,635, filed Dec. 8, 2017, the entirety of which is hereby incorporated by reference and should be considered a part of this specification.

FIELD OF THE DISCLOSURE

The present disclosure relates to methods and systems for delivering a respiratory flow therapy to a patient. In particular, the present disclosure relates to a heater plate assembly configured for heating water in a humidification chamber to humidify and heat gases delivered to the patient.

BACKGROUND

Breathing assistance apparatuses are used in various environments such as hospital, medical facility, residential care, or home environments to deliver a flow of gases to users or patients. A breathing assistance or respiratory therapy apparatus (collectively, “respiratory apparatus” or “respiratory devices”) may deliver ambient air. A breathing assistance or respiratory therapy apparatus may also optionally deliver supplementary oxygen or other gases with ambient air, and/or include a humidification apparatus to deliver heated and humidified gases. A respiratory apparatus may allow adjustment and control over characteristics of the gases' flow, including flow rate, temperature, gases concentration, humidity, pressure, etc. Sensors, such as thermistors and/or pressure sensors are used to measure characteristics of the gases flow.

SUMMARY

This disclosure describes examples of a respiratory humidification system that humidifies a flow of respiratory gases supplied to a user. The system can include a main housing that receives a humidification chamber, a heating plate included in the main housing and positioned to contact the humidified chamber and transfer heat to the humidifier chamber, and a heating element that provides heat to the heating plate. The heating element can include a temperature sensor disposed in a central region of the heating element. Disposing the temperature sensor in the central region can reduce a likelihood that conductors of the heating element will cause an incorrect temperature measurement by the temperature sensor.

The heater plate assembly can include a layer of adhesive between the heating plate and the heating element. If too little adhesive is applied, the bonding will not hold. An excess amount of adhesive, however, may increase a distance and thermal insulation between the heating plate and the heating element, thereby reducing the efficiency of heat transfer from the heating element to the heating plate. An excess amount of adhesive may also result in an uneven heat transfer surface. This may cause a controller of the humidification system to send a power signal to energize the heating element to a much higher temperature than the target temperature of the heating plate. An excess amount of adhesive may also spill into other parts of the heater plate assembly where it may be undesirable to have adhesive. For example, the adhesive may block a gap or opening intended to remain open or otherwise increase risks of malfunction of the humidification system.

The present disclosure provides a heater plate assembly that allows any excess adhesive to flow into one or more relief channels thereby mitigating the drawbacks of using an excess amount of adhesive. The relief channel(s) can allow a more even heat transfer surface between the heating element and the heating plate, and/or reduce a thickness of the adhesive and thus a distance between the heating plate and the heating element, without compromising the secure bonding between the heating plate and the heating element by a sufficient amount of adhesive. Accordingly, the one or more relief channels can improve heat transfer from the heating element to the heating plate. Improving the heat transfer between the heating element and the heating plater can allow a lower heating element temperature to be used to achieve the same heat transfer between the heating element and the humidification chamber. Additionally, the relief channels result in a more consistent thickness of the glue for each heater plate assembly. Having a consistent thickness of glue allows for more accurate control of the heating of the humidification chamber. The relief channel(s) can also improve safety in using the humidification system.

In some configurations, a respiratory humidification system which humidifies a flow of respiratory gases supplied to a user can include a main housing that receives a humidification chamber, a heating plate included in the main housing and positioned to contact the humidifier chamber and transfer heat to the humidifier chamber, and a heating element that provides heat to the heating plate. The system can include a shroud that couples the heating element and the heating plate with the main housing, the shroud comprising at least one relief channel that is shaped to receive excess adhesive when the heating element is adhered to the heating plate.

In some configurations, the heating element can include a substrate, a temperature sensor disposed in a central region of the substrate, and a single resistive track wound in turns on the substrate, except that in some configurations, the single resistive track is not disposed in the central region of the substrate. The system of the preceding two paragraphs can be implemented together with any combination of the following features: the humidification chamber can be removable; the single resistive track can be in an electrically series configuration; the temperature sensor can include a plurality of temperature sensors; the temperature sensor can connect with conductors that terminate proximate an end of the substrate; two ends of the single resistive track can terminate proximate the end of the substrate; a flexible PCB connected to the conductors can be included; a flexible PCB connected to the conductors and the two ends of the single resistive track can be included; placement of the temperature sensor in the central region can reduce a likelihood that the single resistive track will cause an incorrect measurement by the temperature sensor; the single resistive track can be a thick film printed track; the substrate can be a ceramic substrate, a part of a printed circuit board (PCB), an aluminum oxide ceramic substrate, a ceramic substrate, a mica substrate, a KAPTON™ substrate, a plastic substrate, or a silicone substrate; a shroud can be included that is coupled with the heating element and the heating plate; the shroud can include legs that attach the shroud to the main housing; and potting can be included that fills at least part of the shroud and at least partially encapsulates the heating element; the at least one relief channel can be recessed into the shroud; the at least one relief channel can be substantially around a perimeter of the shroud; the shroud can comprise a recessed region that receives the heating element, the recess comprising an uneven or textured surface; the at least one relief channel can comprise four relief channels; the at least one relief channel can comprise a curved shape; the at least one relief channel can comprise recessed corners that receive the heating element; the at least one relief channel can be adjacent to the heating element; the at least one relief channel can substantially surround the heating element; the at least one relief channel can comprise a groove.

In some configurations, the heating element can include a substrate and a resistive track on the substrate. In some configurations, the heating element can include a substrate and a resistive track wound in turns on the substrate. The resistive track may not be disposed in a central region of the substrate. The heating element can further comprise a temperature sensor disposed on the substrate. The temperature sensor can be spaced from the resistive track. A spacing between the temperature sensor and the resistive track can be greater than spacing between portions of the resistive track. A spacing between the temperature sensor and the resistive track can be 1 cm to 20 cm, or 2 cm to 15 cm, or 5 cm to 10 cm, or 6 cm to 7 cm. The temperature sensor can comprise a plurality of temperature sensors. The temperature sensor can connect with conductors that terminate proximate an end of the substrate. The system can comprise a flexible PCB connected to the conductors. The flexible PCB can be connected to the conductors and the resistive track. The temperature sensor can be placed in the central region of the substrate so as to reduce a likelihood of the resistive track causing an incorrect measurement by the temperature sensor. The resistive track can be in an electrically in-series configuration. The resistive track can be a single resistive track. Two ends of the single resistive track can terminate proximate the end of the substrate. The resistive track can comprise a thick film printed track. The substrate can be a part of a printed circuit board (PCB), a ceramic substrate, an aluminum oxide ceramic substrate, a fiberglass substrate, a mica substrate, a KAPTON™ substrate, a plastic substrate, or a silicone substrate. The shroud can be coupled with the heating element and the heating plate, the shroud comprising legs that attach the shroud to the main housing. The system can further comprise potting that fills at least part of the shroud and at least partially encapsulates the heating element. The at least one relief channel can be recessed into the shroud. The at least one relief channel can be substantially around a perimeter of the shroud. The shroud can comprise a recessed region that receives the heating element, the recess comprising an uneven or textured surface. The at least one relief channel can comprise four relief channels. The at least one relief channel can comprise a curved shape. The at least one relief channel can comprise recessed corners that receive the heating element. The at least one relief channel can be adjacent to the heating element. The at least one relief channel can substantially surround the heating element. The at least one relief channel can comprise a groove.

In some configurations, a respiratory humidification system which humidifies a flow of respiratory gases supplied to a user can include a main housing that receives a humidification chamber, a heating plate included in the main housing and positioned to contact the humidifier chamber and transfer heat to the humidifier chamber, and a heating element that provides heat to the heating plate. The system can include a shroud comprising a recessed region that receives the heating element, the recessed region comprising at least one relief channel that receives excess adhesive when the heating element is adhered to the heating plate.

In some configurations, the heating element can include a substrate, a temperature sensor disposed in a central region of the substrate, and a plurality of heating pads disposed on the substrate about the central region and not in the central region. The heating pads can be electrically connected in series, such that placement of the heating pads away from the central region can reduces a likelihood that the heating pads will cause an incorrect measurement by the temperature sensor. In some configurations, the heating element can include a single resistive track wound in turns on the substrate.

The system of the preceding two paragraphs can be implemented together with any combination of the following features: the humidification chamber can be removable; the temperature sensor can include a plurality of temperature sensors; the temperature sensor can connect with conductors that terminate proximate an end of the substrate; a flexible PCB can be included that is connected to the conductors; a conductive strip can be included that is connecting the heating pads; two ends of the conductive strip can terminate proximate the end of the substrate; a flexible PCB can be included that is connected to the conductors and the two ends of the single resistive track; the heating element can further comprise a temperature sensor disposed on the substrate; the temperature sensor can be spaced from the resistive track; a spacing between the temperature sensor and the resistive track can be greater than spacing between portions of the resistive track; a spacing between the temperature sensor and the resistive track can be 1 cm to 20 cm, or 2 cm to 15 cm, or 5 cm to 10 cm, or 6 cm to 7 cm; the heating pads can be thick film printed pads; the substrate can be a ceramic substrate, a part of a printed circuit board (PCB), an aluminum oxide ceramic substrate, a fiberglass substrate, a mica substrate, a KAPTON™ substrate, a plastic substrate, or a silicone substrate; a shroud can be included that is coupled with the heating element and the heating plate; the shroud can include legs that attach the shroud to the main housing; the shroud can include walls around a void, where the void can be above the heating element or below the heating element; and potting can be included between the walls so as to fill the void and at least partially encapsulate the heating element; the at least one relief channel can be recessed into the shroud; the at least one relief channel can be substantially around a perimeter of the shroud; the shroud can comprise a recessed region that receives the heating element, the recess comprising an uneven or textured surface; the at least one relief channel can comprise four relief channels; the at least one relief channel can comprise a curved shape; the at least one relief channel can comprise recessed corners that receive the heating element; the at least one relief channel can be adjacent to the heating element; the at least one relief channel can substantially surround the heating element; the at least one relief channel can comprise a groove.

For purposes of summarizing the disclosure, certain aspects, advantages, and novel features of the inventions have been described herein. It is to be understood that not necessarily all such advantages can be achieved in accordance with any particular embodiment of the invention. Thus, the invention can be embodied or carried out in a manner that achieves or optimizes one advantage or group of advantages as taught herein without necessarily achieving other advantages as can be taught or suggested herein.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain examples are described herein, those of skill in the art will appreciate that the disclosure extends beyond the specifically disclosed examples and/or uses and obvious modifications and equivalents thereof. Thus, it is intended that the scope of the disclosure herein disclosed should not be limited by any particular examples described herein.

I. Overview of Example Flow Therapy Apparatuses

Figure 1A:
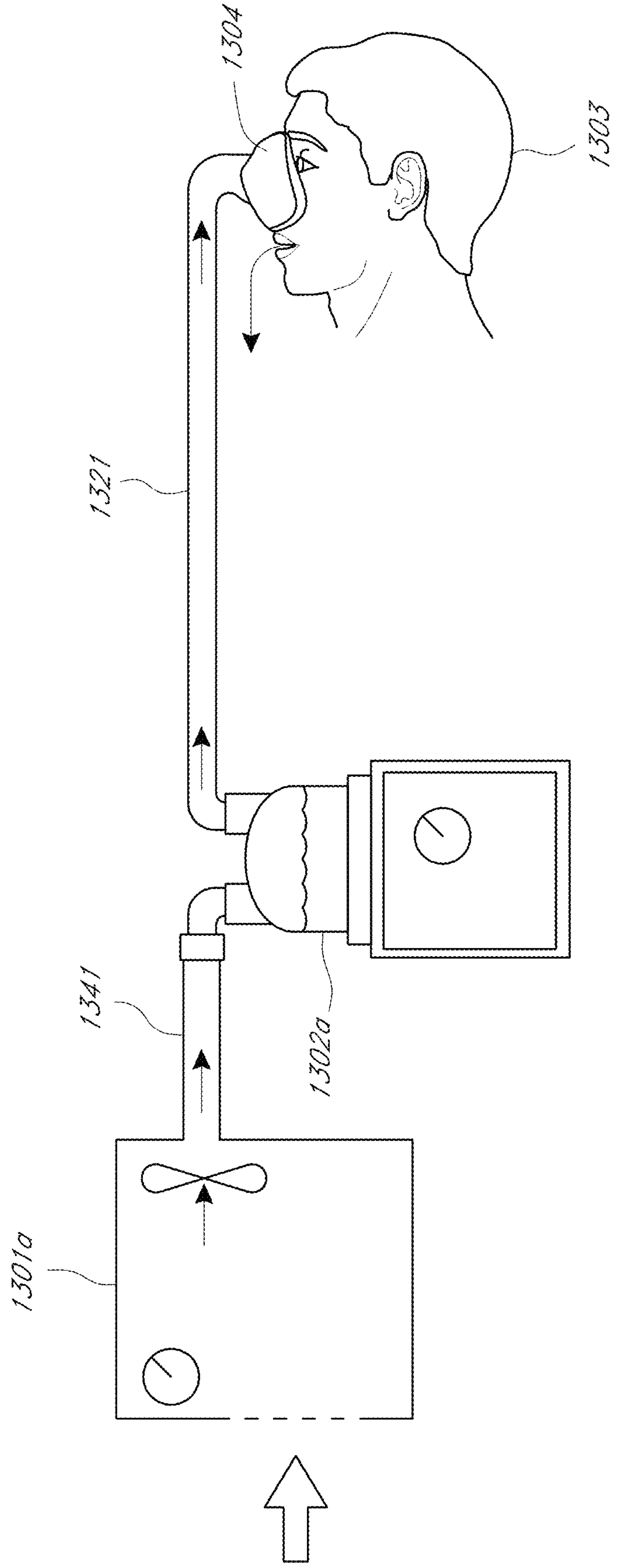
FIGS. 1A through 3B show example respiratory devices configured to provide respiratory therapy to a user.

FIGS. 1A through 1D show example respiratory devices that can implement the features described herein. Each of the various systems described in FIGS. 1A-1D can be used with the specific features described later in this application. Turning to FIG. 1A, a schematic view of a user 1303 receiving air from a modular assisted breathing unit and humidifier system is shown. A conduit 1341 provides pressurized air from an assisted breathing unit or blower unit 1301*a* to a humidifier chamber 1302*a*. A heater plate assembly in the modular assisted breathing unit and humidifier system can be in contact with the humidifier chamber 1302*a* to heat water in the chamber 1302*a*. Gases passing through the humidifier chamber 1302*a* can be humidified and heated. Humidified, heated and pressurized gases exit the humidifier chamber 1302*a* via an inspiratory conduit 1321, and are provided to the patient or user 1303 via a user interface 1304. The user interface 1304 shown in FIG. 1A is a nasal mask, which covers the nose of the user 1303. However, it should be noted that in systems of these types, a full face mask, nasal cannula, tracheostomy fitting, nasal pillows, oral interface, or any other suitable user interface could be substituted for the nasal mask shown.

Figure 1B:
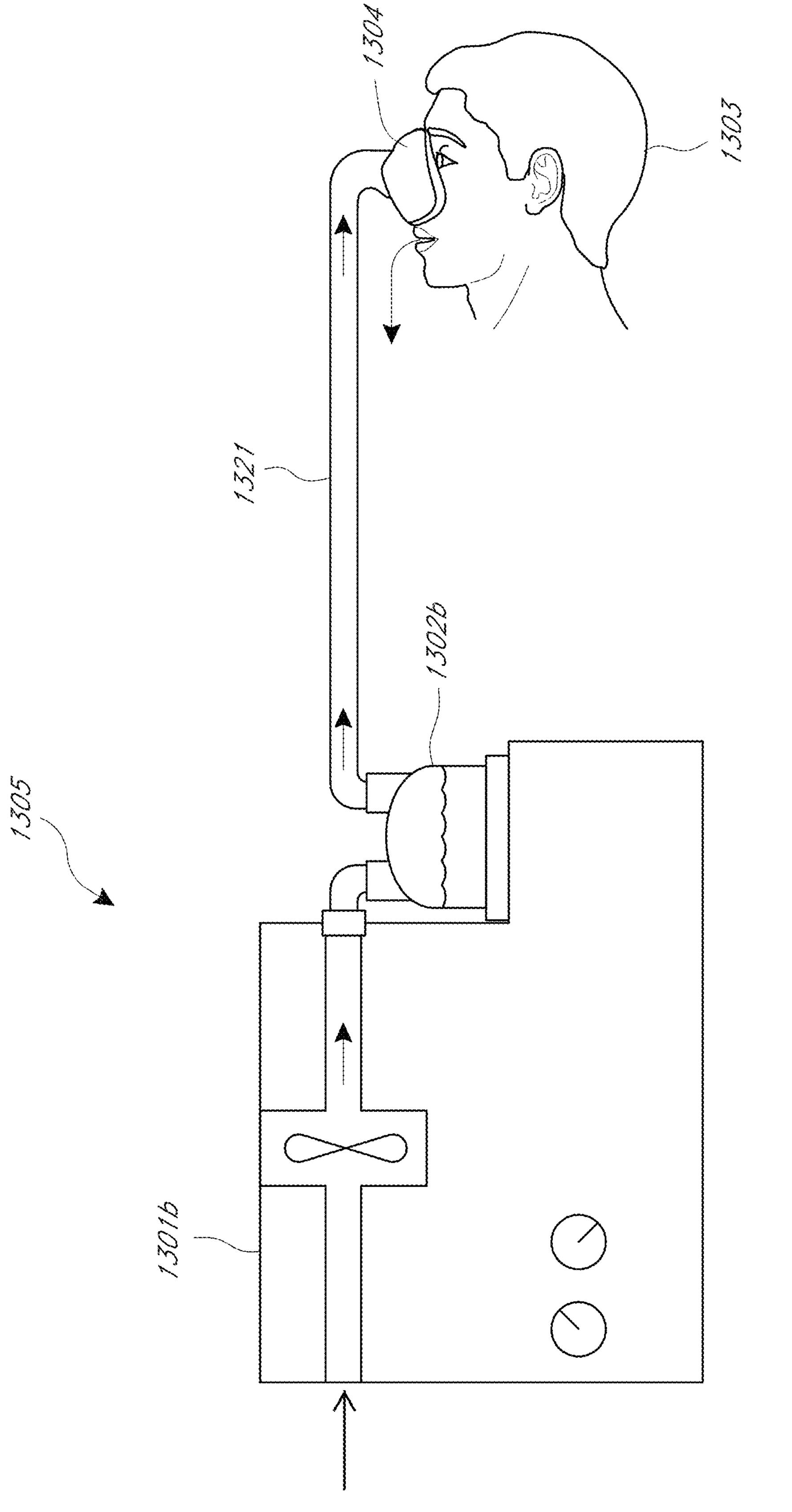

FIG. 1B shows a schematic view of the user 1303 receiving air from an integrated blower/humidifier unit 1305. The system generally operates in the same manner as the modular system shown in FIG. 1A except that a humidifier chamber 1302*b* has been integrated with a blower unit 1301*b* to form the integrated unit 1305. Accordingly, the integrated blower/humidifier unit 1305 can include a heater plate assembly configured to heat water in the chamber 1302*b*. An example of an integrated unit is described in PCT application WO2008/056993, which is hereby incorporated by reference in its entirety.

Assisted Breathing Unit

An example assisted breathing unit or integrated unit 1306 will now be described with reference to FIGS. 1C and 1D.

The integrated unit 1306 can include two main parts: an assisted breathing or blower unit 1307 and a humidification unit 1331. When in use, the humidification unit 1331, which can include a humidification chamber, generally is enclosed within an enclosure that is formed in an external casing of the integrated unit 1306. In the illustrated configuration, the top part of the humidification unit 1331 is not enclosed within the enclosure 1342. The blower unit 1307 can include a heater plate assembly in contact with the humidification unit 1331 to heat water inside the humidification chamber.

The blower unit 1307 has an outer shell that generally is a rectangular block with substantially vertical side and rear walls, and a front face that is angled slightly rearwards. In the illustrated embodiment, the walls, base and top surface are all manufactured and connected as far as possible to minimize the occurrence of seams. Any necessary seams can be sealed. This outer shell generally encloses the working parts of the blower unit 1307 and forms part of the blower unit 1307.

Figure 1C:
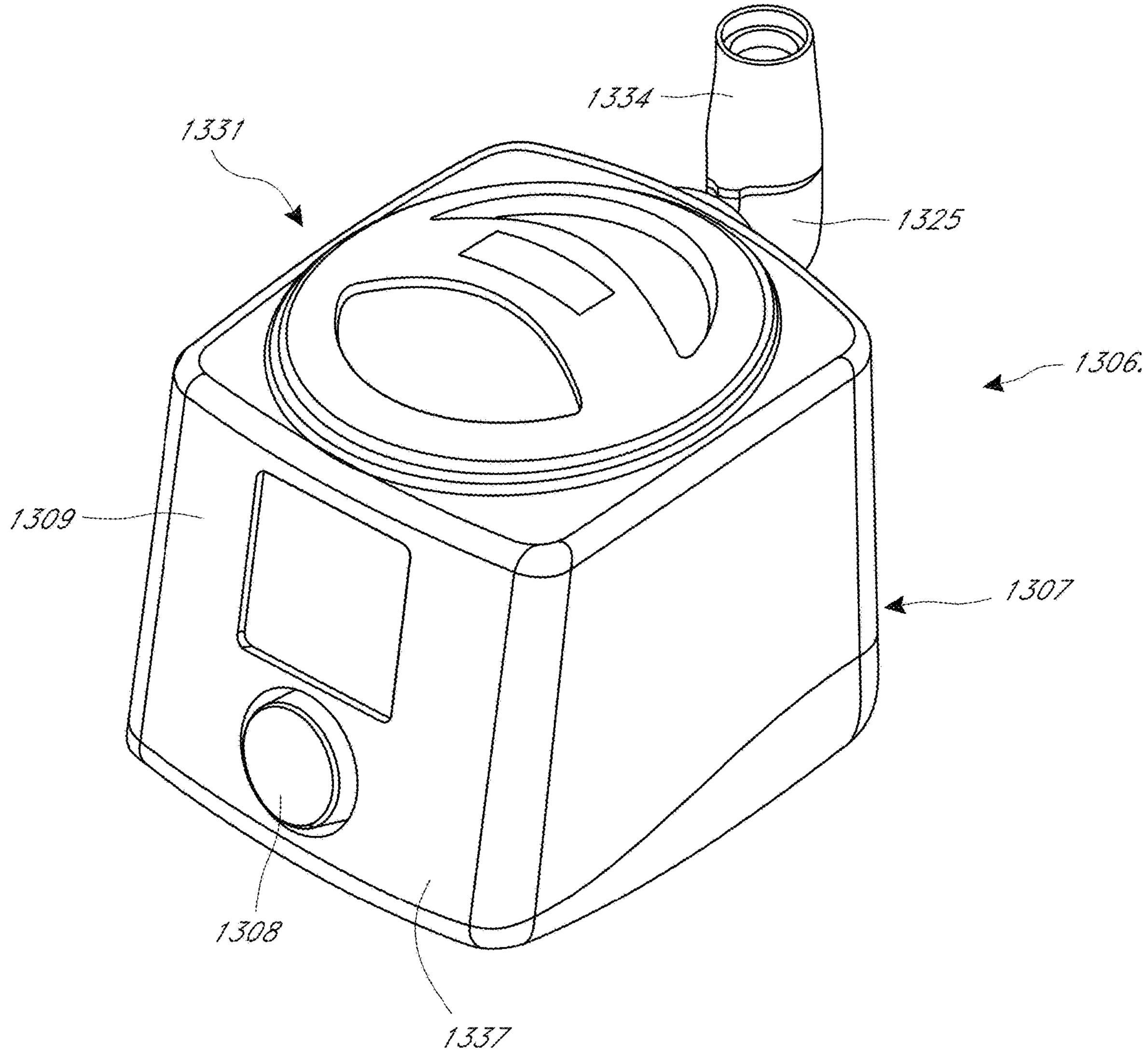
Figure 1D:
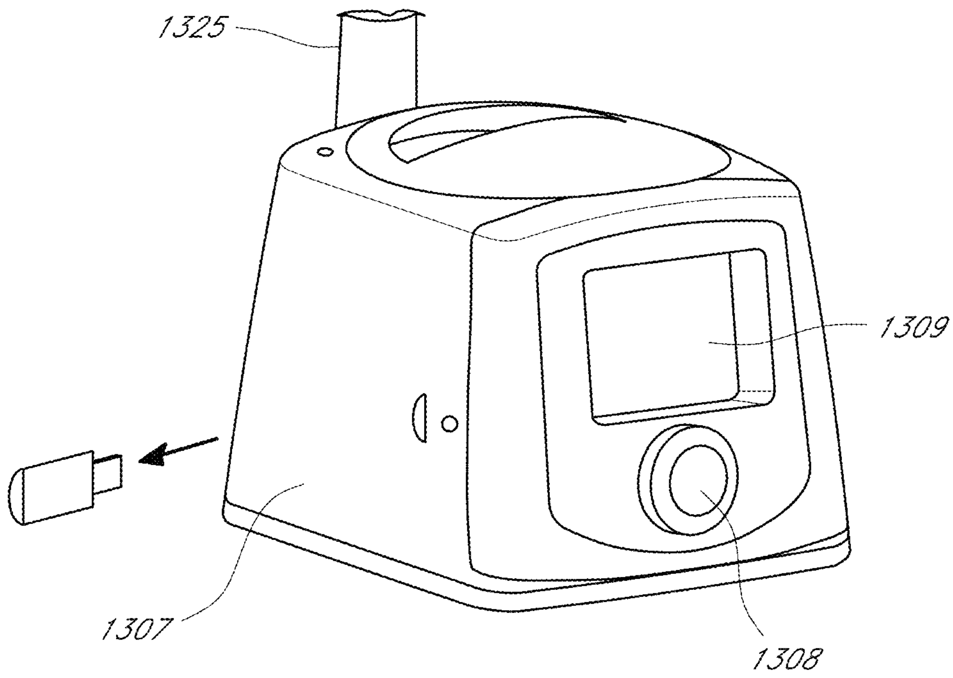

As shown in FIGS. 1C and 1D, a user interface is located on the lower section of the front face of the illustrated integrated unit 1306 with a control display 1309 located directly above the user interface. The user interface can include a control knob 1308. A patient outlet 1325 is shown passing out of the rear wall of the integrated unit 1306. In the illustrated embodiment, in use the free end of the outlet 1325 faces upwards for ease of connection. However, the patient outlet 1325 can be rotated to one side or to the other side to move or align it in a more convenient position for storage or to provide a more convenient use position.

The illustrated patient outlet 1325 is adapted to allow both pneumatic and electrical connection to one end of a conduit, for example, the conduit (such as the inspiratory conduit 1321 of FIG. 1B), that extends between the unit 1306 and a patient interface, for example, the interface 1304 of FIG. 1B. An example of the type of connector that can be used and the type of dual connection that can be made is described in U.S. Pat. No. 6,953,354, which is hereby incorporated by reference in its entirety. It should be noted that for the purposes of reading this specification, the patient interface generally can be thought of as including both the interface 1304 and the inspiratory conduit 1321 where it would be appropriate to read it in this manner.

The integrated unit 1306 can include an inlet vent or inlet port (not shown) to draw air in from atmosphere. The inlet port or vent could also be a connector adapted to receive gases from a wall source, pressure bottle or the like. The integrated unit 1306 can also include a mechanism for providing a pressurized air flow from the inlet vent to the humidification unit 1331. The pressurized air flow mechanism can include a fan unit. The vent can be located wherever is convenient on the external surface of the integrated unit 1306. The vent can be located on the rear face of the blower unit 1307.

The air is ducted or otherwise directed along an air path through the casing of the blower unit 1307 and delivered to the humidification unit 1331, where it is humidified and heated by the heated water, before passing out of the humidification unit 1331 and onwards to the patient outlet 1325 on the blower unit 1307. The heated humidified gas then passes to the user 1303 via the inspiratory conduit 1321 and a patient interface, which can include any suitable patient interface examples disclosed herein.

The outlet port or patient outlet 1325 is adapted to enable both pneumatic attachment of the inspiratory conduit 1321 and electrical connection via an electrical connector. In FIG. 1C, a conduit connector 1334 that would normally be fitted to the end of the inspiratory conduit 1321 is shown connected to the patient outlet 1325. The outlet port or outlet connection does not have to be via the housing of the integrated unit 1306, as in the illustrated embodiment. Instead, the connection for the inspiratory conduit 1321 could be located directly on an outlet from humidification unit 1331. The illustrated form and variations generally can be referred to as connection mechanisms.

The integrated unit 1306 also contains electronic circuitry enclosed within the casing, which at least partly comprises a controller, such as a microprocessor or the like, and which provides control signals to control the output or outputs of at least the blower unit 1307, and preferably other items such as the humidification unit 1331. The control circuitry also can be adapted to receive signals from sensors in the system (for example, pressure, flow, humidity and temperature signals from these sensors as applicable) and to alter outputs from the control circuitry accordingly. The control circuitry also receives signals from user controls as the user controls are manipulated by a user and alters the output signals accordingly.

Figure 2A:
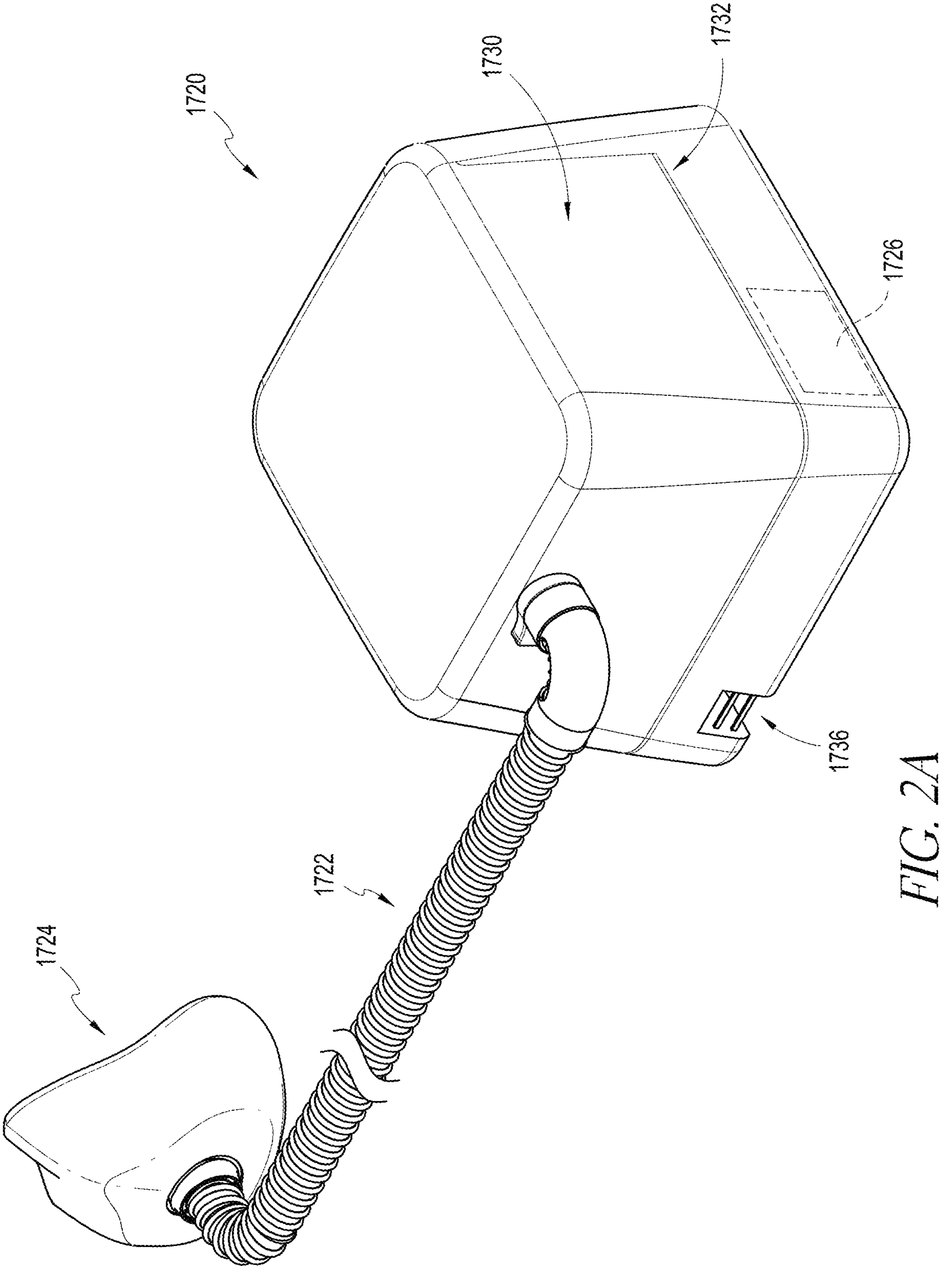

FIGS. 2A through 2D show additional respiratory devices that can implement the features described herein. Again, each of the various systems described in FIGS. 2A-2D can be used with the specific features described later in this application. Turning to FIG. 2A, a breathing assistance apparatus 1720 is shown that is arranged and configured in accordance with certain features, aspects and advantages of the present invention. In the illustrated configuration, the breathing assistance apparatus 1720 is connected to an inspiratory conduit 1722 and the inspiratory conduit 1722 is connected to a patient interface 1724, such as a breathing mask or the like. Any suitable patient interface 1724 can be used.

The breathing assistance apparatus 1720 is configured to deliver a flow of pressurized breathing gases to the user through the conduit 1722 and the patient interface 1724. Accordingly, the illustrated breathing assistance apparatus 1720 can include a blower unit 1726, which has been schematically illustrated in FIG. 2A. The blower unit 1726 can have any suitable construction. The blower unit draws ambient air into the breathing assistance apparatus 1720 and generates the flow of pressurized breathing gases.

Figure 2B:
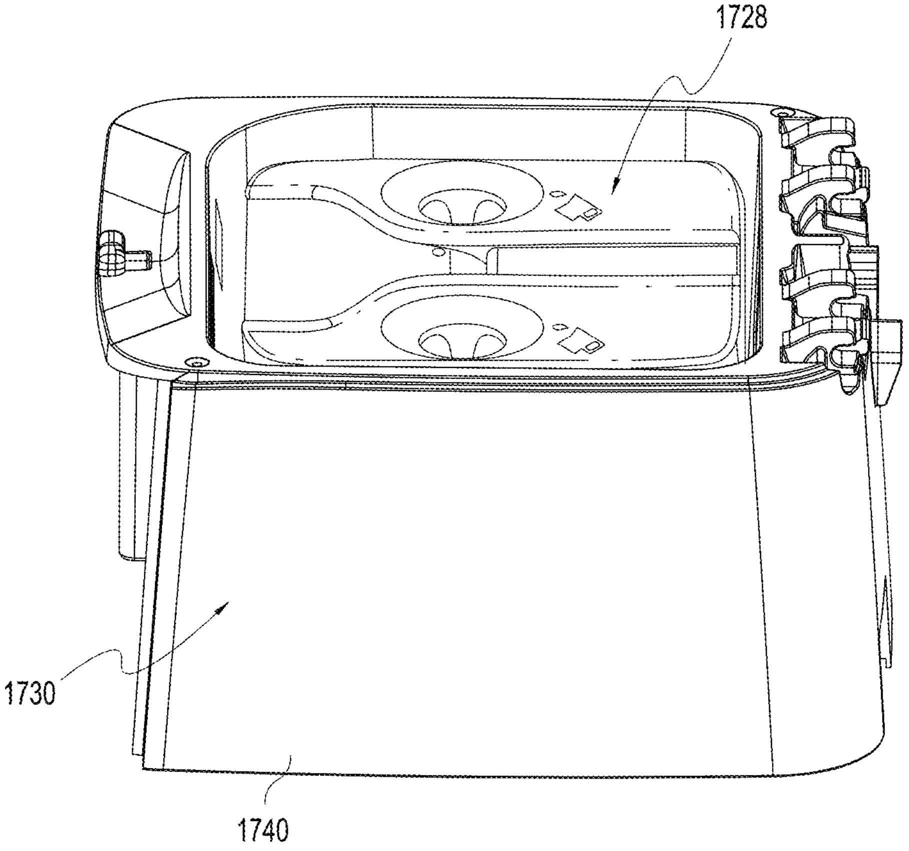
Figure 2C:
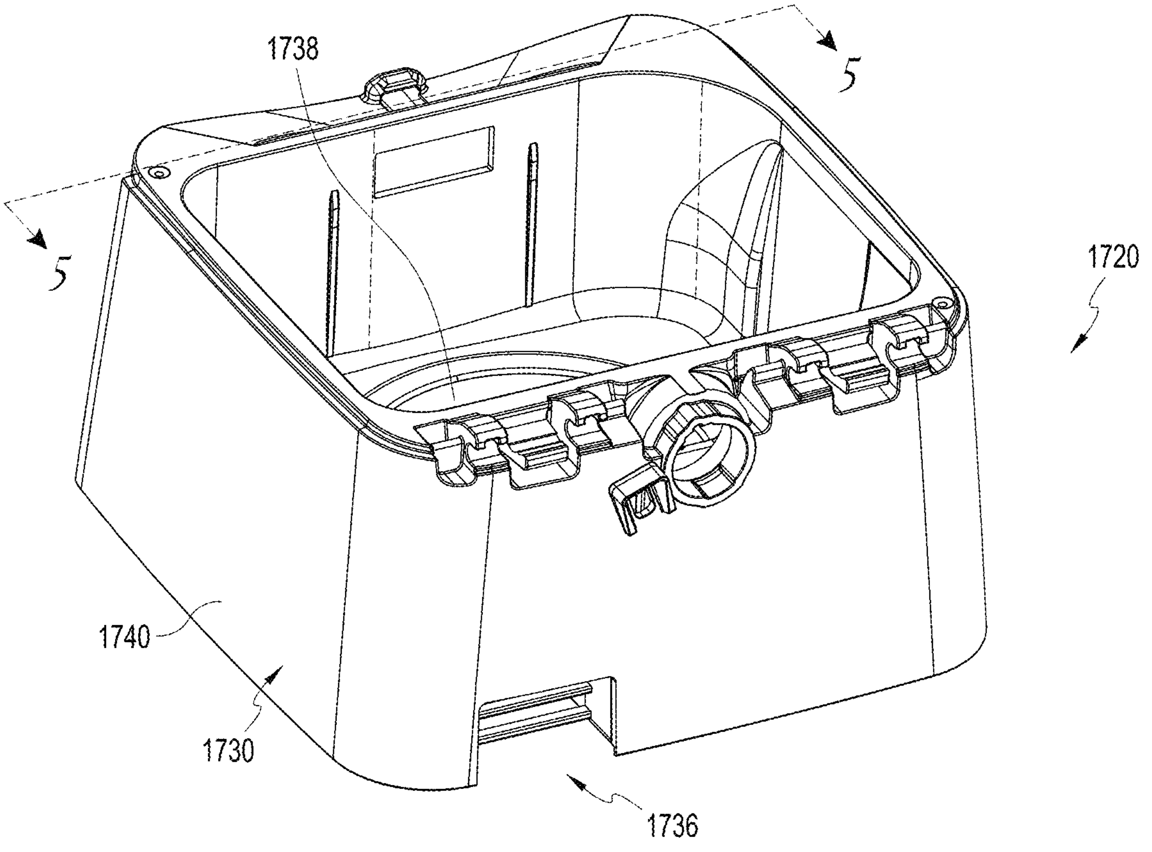

The breathing assistance apparatus 1720 also is configured to humidify the flow of pressurized breathing gases prior to deliver to the user. Accordingly, as illustrated in FIG. 2B, the illustrated breathing assistance apparatus 1720 also can include a humidification chamber 1728. The humidification chamber 1728 can be removable from the breathing assistance apparatus 1720. Any suitable construction can be used for the humidification chamber 1728. The humidification chamber 1728 can be configured to contain a volume of liquid, such as water. The flow of pressurized breathing gases can pass over the volume of liquid en route to the user such that the flow of pressurized breathing gases can increase in humidity.

Figure 2D:
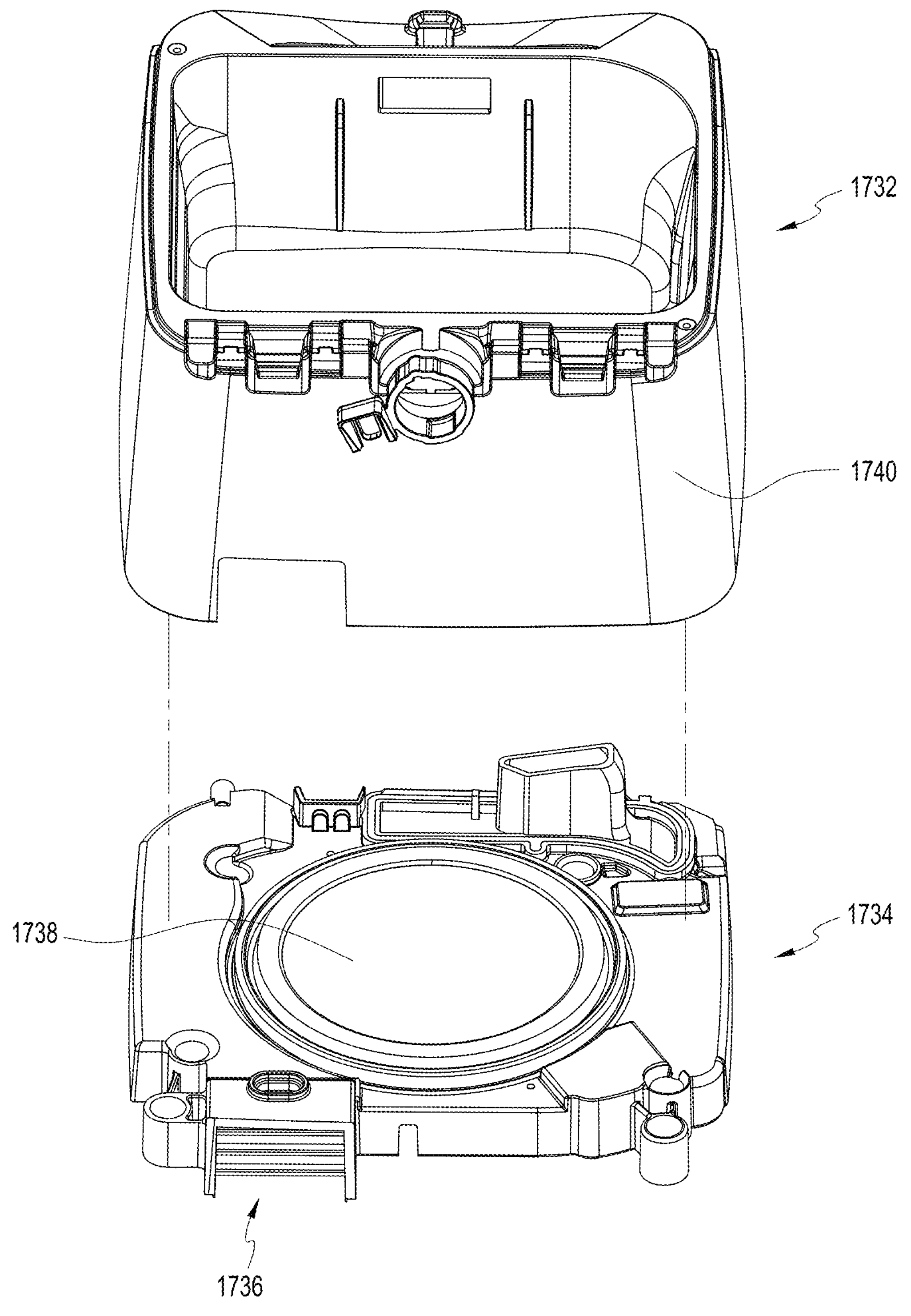

As illustrated, the breathing assistance apparatus 1720 generally can include a main body 1730. With reference to FIG. 2D, the main body 1730 can include an upper housing 1732 and a lower housing 1734. The upper housing 1732 and the lower housing 1734 can be secured together in any suitable manner. In some configurations, the bottom of the lower housing 1734 can be enclosed by a further cover.

With continued reference to FIG. 2D, the lower housing 1734 can include an air inlet 1736 through which the blower unit 1726 draws air. The blower unit 1726 can be mounted to or within the lower housing 1734. The lower housing 1734 also can support a heater plate assembly 1738. The liquid within the humidification chamber 1728 can be heated through an interaction with the heater plate assembly 1738. In some configurations, the humidification chamber 1728 can rest on a heating plate of the heater plate assembly 1738. Other configurations are possible.

Figure 3A:
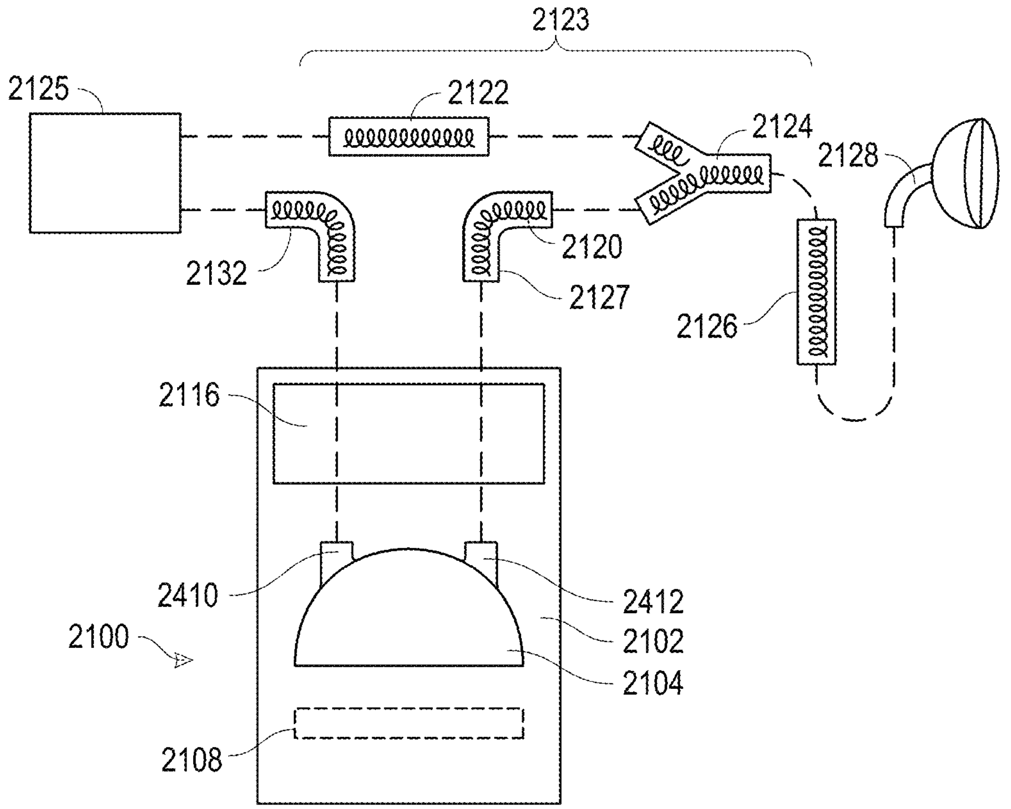
Figure 3B:
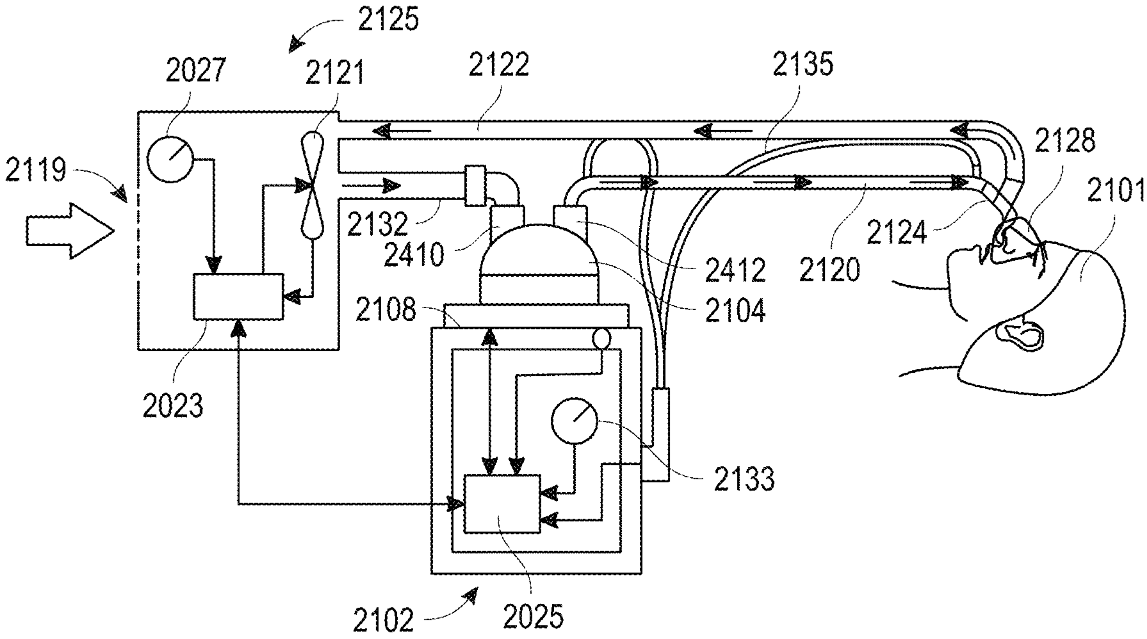

FIGS. 3A and 3B show additional respiratory device examples that can implement the features described herein. Each of the various systems described in FIGS. 3A and 3B can be used with the specific features described later in this application. FIGS. 3A and 3B schematically illustrate examples of a humidification system 2100 that, in some applications, can be used with breathing therapies, positive pressure apparatus, noninvasive ventilation, surgical procedures including but not limited to laparoscopy, and the like. Desirably, the humidification system 2100 can be adapted to supply humidity or vapor to a supply of gases. The humidification system 2100 can be used with ventilators, nasal high flow systems, continuous, variable, or bi-level positive airway pressure (PAP) systems or other form of respiratory therapy. In some configurations, the humidification system 2100 can be integrated into a system that delivers any such types of therapy.

An example of the humidification system 2100 can include a heater base unit 2102 and a humidification chamber 2104. The heater base unit 2102 can comprise a heater plate assembly 2108. The humidification chamber 2104 can be configured to hold a volume of a liquid, such as water. The heater plate assembly 2108 can be configured to heat the volume of liquid held within the humidification chamber 2104 to produce vapor.

The humidification chamber 2104 is removable from the heater base 2102 to allow the humidification chamber 2104 to be more readily sterilized or disposed. The body of the humidification chamber 2104 can be formed from a non-conductive glass or plastics material but the humidification chamber 2104 can also include conductive components. For instance, the humidification chamber 2104 can include a highly heat-conductive base (for example, an aluminum base) contacting or associated with the heater plate assembly 2108 on the heater base unit 2102.

The heater base unit 2102 can also include electronic controls. In this example, the heater base unit 2102 includes a master controller 2025. The master controller 2025 can comprise an electronic, analog, or digital processor or controller. Preferably, the master controller 2025 comprises a microprocessor-based controller configured to execute computer software commands stored in associated memory. In response to user-set humidity or temperature values input via a user interface 2133, for example, and other inputs, the master controller 2025 determines when (or to what level) to energize a heating element of the heater plate assembly 2108 to heat the liquid within the humidification chamber 2104.

The humidification system 2100 also can include a gases supply 2125. In some configurations, the gases supply 2125 can comprise a ventilator, blower unit, or any other suitable source of pressurized gases suitable for breathing or use in medical procedures. The gases supply 2125 can be separate from or combined with the heater base 2102.

For example as shown in FIG. 3B, dry or relatively dry gases, or ambient air, enter the gases supply 2125 through a vent 2119. A fan 2121 can improve gas flow into the gases supply by drawing air or other gases through the vent 2119. The fan 2121 can be, for instance, a variable speed fan, where a controller 2023 controls the fan speed. In particular, the function of the controller 2023 can be controlled by the master controller 2025 in response to inputs from the master controller 2025 and a user-set predetermined required value (preset value) of pressure or fan speed via a dial 2027.

The humidification system also can include a breathing circuit 2123. The breathing circuit 2123 can include an inspiratory conduit 2120. A chamber end of the inspiratory conduit 2120 can be configured to connect to an outlet port 2412 of the humidification chamber 2104. A patient end of the inspiratory conduit 2120 can be configured to connect to the patient, for example, via a patient interface 2128. In some configurations, the inspiratory conduit 2120 can be coupled directly to the patient interface 2128. Any suitable type of the patient interface 2128 can be incorporated. Patient interface is a broad term and is to be given its ordinary and customary meaning to a person of ordinary skill in the art (that is, it is not to be limited to a special or customized meaning) and includes, without limitation, masks (such as tracheal masks, face masks and nasal masks), cannulas, and nasal pillows.

A temperature probe 2135 can connect to the inspiratory conduit 2120 near the patient interface 2128, or directly to the patient interface 2128. The temperature probe 2135 monitors the temperature near or at the patient interface 2128.

A heating element (not shown), for example, a heating element that is associated with the temperature probe or a heating element not associated with a temperature probe, can be used to adjust the temperature of the patient interface 2128 and/or the inspiratory tube 2120 to raise the temperature of the inspiratory conduit 2120 and/or the patient interface 2128 above the saturation temperature, thereby reducing the opportunity for unwanted condensation.

In some configurations in which the gases supply 2125 is separate from the heater base unit 2102, the breathing circuit 2123 can include a supply conduit 2132. A gases supply end of the supply conduit 2132 can be configured to connect to an output of the gases supply 2125. A chamber end of the supply conduit 2132 can be configured to connect to an inlet port 2410 of the humidification chamber 2104.

In some configurations, such as those used with a ventilator, the breathing circuit 2123 also can include an expiratory conduit 2122. A user end of the expiratory conduit 2122 can be configured to connect to the patient interface 2128, and a gases supply end of the expiratory conduit 2122 can be configured to connect to a return of the gases supply 2125. The expiratory conduit 2122 can have a temperature probe and/or heating element, as described above with respect to the inspiratory conduit 2120, integrated with it to reduce the opportunity for condensation. Furthermore, the expiratory conduit 2122 need not return exhaled gases to the gases supply 2125. In some configurations, exhaled gases can be passed directly to ambient surroundings or to other ancillary equipment, such as an air scrubber/filter (not shown). The expiratory conduit 2122 may be omitted altogether.

As shown in FIG. 3A, the user ends of the inspiratory conduit 2120 and the expiratory conduit 2122 can be connected to each other via a Y-piece 2124. The Y-piece 2124 can be connected to a patient supply conduit 2126. In some configurations, the patient supply conduit 2126 can include a catheter mount, for example but without limitation. The patient supply conduit 2126 can be connected to the patient interface 2128. The Y-piece 2124 may couple to the patient interface 2128 without the patient supply conduit 2126 intervening.

In use, the humidification chamber 2104 is installed onto a heating plate of the heater plate assembly 2108. The heater plate assembly 2108 heats liquid, such as water, in the humidification chamber 2104 to produce vapor. Dry or relatively dry gases flow from the gases supply 2125, through the supply conduit 2132, and into the humidification chamber 2104 through the inlet port 2410. The gases pass over the liquid in the humidification chamber 2104 and become humidified by the vapor. Humidified gases exit the humidification chamber 2104 through the outlet port 2412 and flow through the inspiratory conduit 2120 to a patient 2101. Gases exhaled by the patient 2101 may be returned to the gases supply 2125 through the expiratory conduit 2122. Any or all of the components of the breathing circuit 2123 can include a heating element, for example, a heating wire 2127, to help maintain the gases at a desired temperature and to reduce the likelihood of significant condensation formation in the conduits.

Before use, an operator, such as medical personnel, will connect the various components to set up the humidification system 2100. Because of the variety of components and number of connections that are made, setup of the humidification system 2100 can be a complex process. In some instances, special training is provided to improve the likelihood of correct setup. The humidification system 2100 can include various features to simplify the setup process and reduce the likelihood of an incorrect setup. For example, components of the humidification system 2100 can include features to provide for easier and more secure connection between components, promote correct connections, and reduce the number of connections needed to be made manually or separately.

Figure 4A:
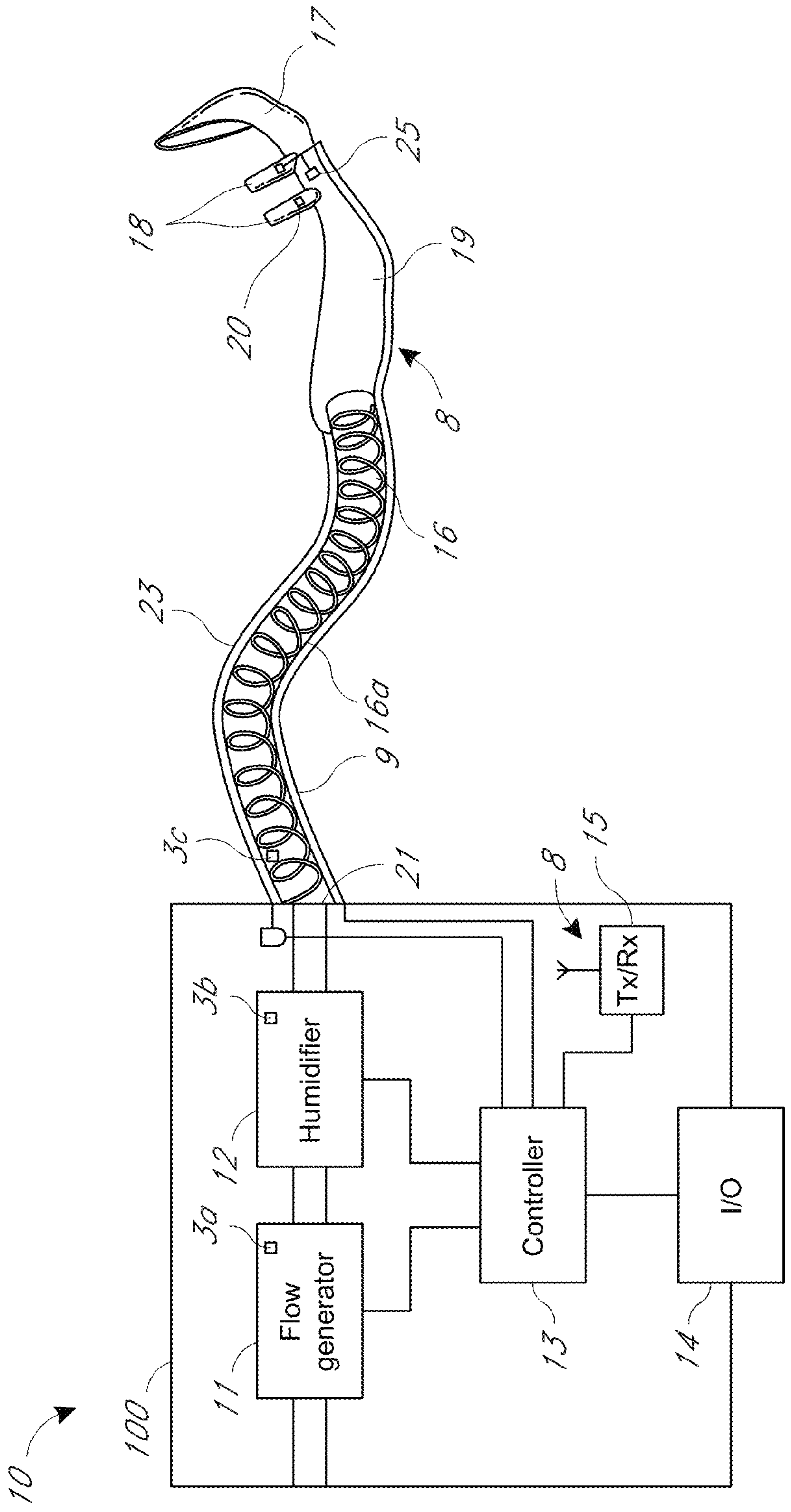
FIG. 4A shows schematically an additional example respiratory system configured to provide a respiratory therapy to a user.
Figure 4B:
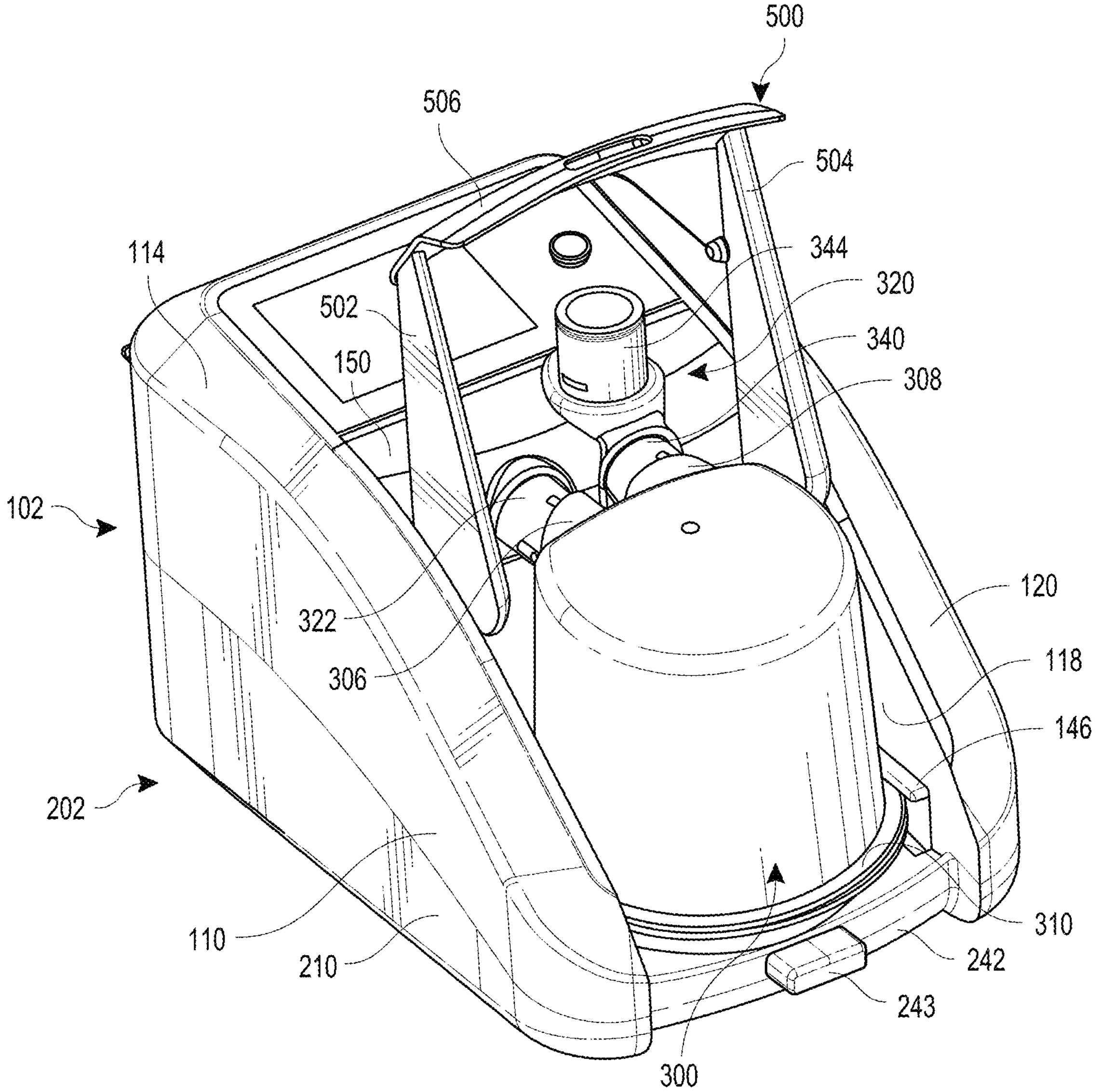
FIG. 4B is a front left perspective view of an example respiratory device with a humidification chamber in position and a raised handle/lever.
Figure 4C:
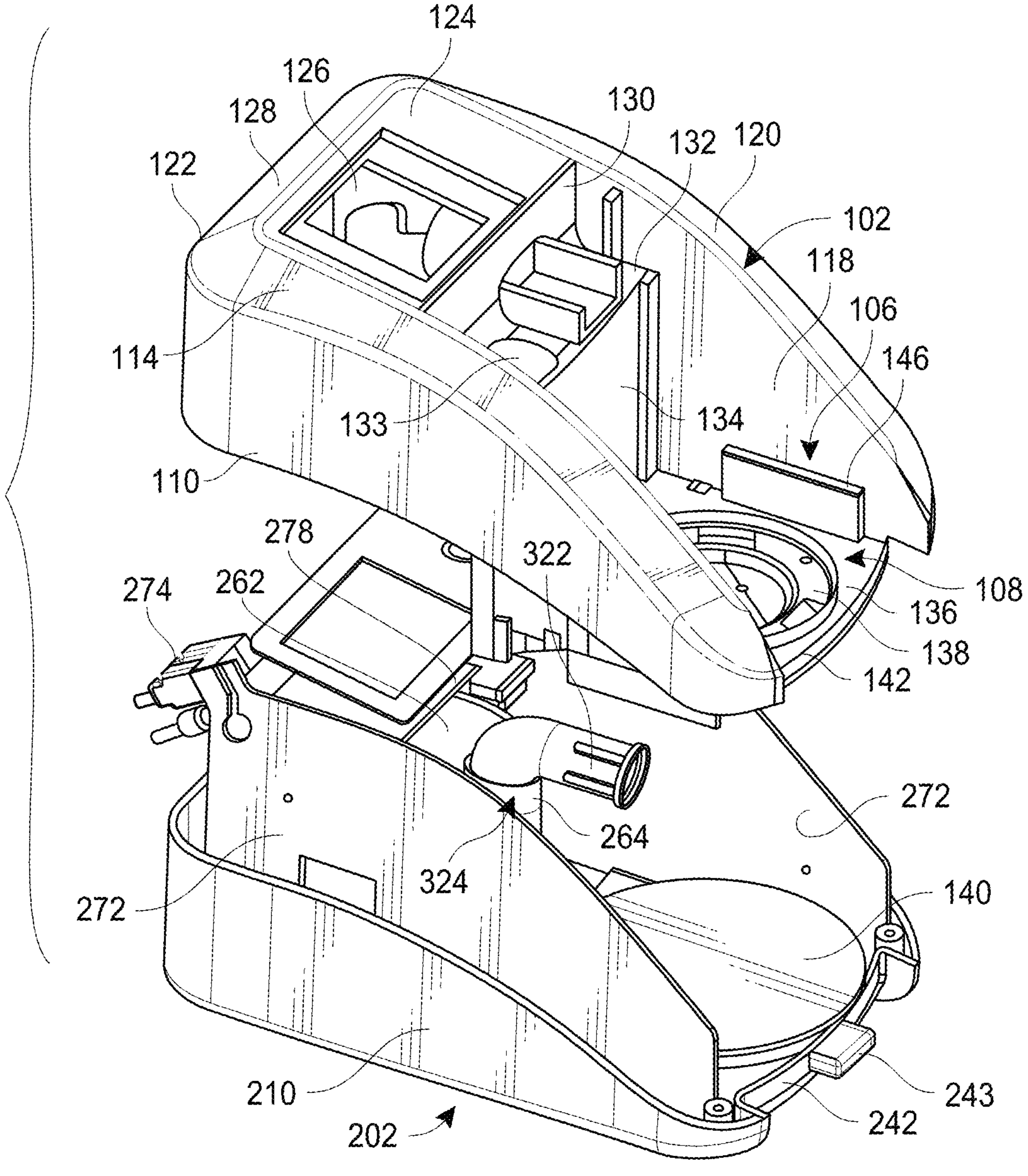
FIG. 4C is an exploded view of upper and lower chassis components of a main housing of the respiratory device of FIG. 2.

A schematic representation of an example respiratory system 10 is provided in FIG. 4A. The respiratory system 10 can include a main device housing 100. The main device housing 100 can contain a blower unit 11 that can be in the form of a motor/impeller arrangement, an optional humidifier or humidification chamber 12, a controller 13, and a user interface 14. The user interface 14 can include a display and input device(s) such as button(s), a touch screen, a combination of a touch screen and button(s), or the like. The controller 13 can include one or more hardware and/or software processors and can be configured or programmed to control the components of the apparatus, including but not limited to operating the blower unit 11 to create a flow of gases for delivery to a patient, operating the humidification chamber 12 (if present) to humidify and/or heat the gases flow, receiving user input from the user interface 14 for reconfiguration and/or user-defined operation of the respiratory system 10, and outputting information (for example on the display) to the user. The user can be a patient, healthcare professional, or others.

With continued reference to FIG. 4A, an inspiratory conduit 16 can be coupled to a gases flow outlet 21 in the main device housing 100 of the respiratory system 10, and be coupled to a patient interface 17, such as a non-sealing interface like a nasal cannula with a manifold 19 and nasal prongs 18. The inspiratory conduit 16 can also be coupled to a face mask, a nasal mask, a nasal pillow mask, an endotracheal tube, a tracheostomy interface, or others.

The gases flow can be generated by the blower unit 11, and may be humidified, before being delivered to the patient via the inspiratory conduit 16 through the patient interface 17. The controller 13 can control the blower unit 11 to generate a gases flow of a desired flow rate, and/or one or more valves to control mixing of air and oxygen or other breathable gas. The controller 13 can control a heating element beneath the humidification chamber 12 to heat the gases to a desired temperature that achieves a desired level of temperature and/or humidity for delivery to the patient. The inspiratory conduit 16 can have a heating element 16*a*, such as a heater wire, to heat gases flow passing through to the patient. The heating element 16*a* can also be under the control of the controller 13.

The system 10 can use ultrasonic transducer(s), thermistor (s), pressure sensor(s), temperature sensor(s), humidity sensor(s), or other sensors, in communication with the controller 13, to monitor characteristics of the gases flow and/or operate the system 10 in a manner that provides suitable therapy. The gases flow characteristics can include gases' concentration, flow rate, pressure, temperature, humidity, or others. The sensors 3*a*, 3*b*, 3*c*, 20, 25, such as flow, temperature, humidity, and/or pressure sensors, can be placed in various locations in the main device housing 100, the inspiratory conduit 16, and/or the patient interface 17. The controller 13 can receive output from the sensors to assist it in operating the respiratory system 10 in a manner that provides suitable therapy, such as to determine a suitable target temperature, flow rate, and/or pressure of the gases flow. Providing suitable therapy can include meeting a patient's inspiratory demand.

The system 10 can include a wireless data transmitter and/or receiver, or a transceiver 15 to enable the controller 13 to receive data signals 8 in a wireless manner from the operation sensors and/or to control the various components of the system 10. Additionally, or alternatively, the data transmitter and/or receiver 15 can deliver data to a remote server or enable remote control of the system 10. The system 10 can include a wired connection, for example, using cables or wires, to enable the controller 13 to receive data signals 8 from the operation sensors and/or to control the various components of the system 10.

The respiratory system 10 can be used in a variety of applications. For instance, the respiratory system 10 can be used in any of the following respiratory devices: a continuous positive air pressure (CPAP) device, a ventilator, a humidifier, a high flow therapy device, a surgical humidifier (for example, an insufflator), combinations of the same, or the like.

CPAP treatment of obstructive sleep apnea involves the delivery of pressurized, breathable gas, usually air, to a user's airways using an inspiratory conduit and a patient interface, such as a mask. The gas pressures employed for CPAP typically range from about 4 cm $H_2O$ to about 28 cm $H_2O$ at flow rates of up to about 180 L/min (measured at the patient interface), depend upon the requirements of the user. The pressurized gas acts as a pneumatic splint for the airway of the user. As such, the pressurized gas reduces the likelihood of collapsing of the airway.

"High flow therapy" as used in this disclosure may refer to delivery of gases to a user through an unsealed nasal cannula at a flow rate of greater than or equal to about 10 liters/minute (10 LPM). In some configurations, "high flow" therapy refers to administration of gas to the airways of a patient at a relatively high flow rate. In some configurations, the relatively high flow rate meets or exceeds the peak inspiratory demand of the user. In other configurations, the high flow rate may not meet or exceed the peak inspiratory demand of the user. The flow rates used to achieve "high flow" may be any of the flow rates listed below. For example, in some configurations, for an adult patient "high flow therapy" may refer to the delivery of gases to a user at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may deliver gases to the patient at a flow rate of between about 1 LPM and about 100 LPM, or at a flow rate in any of the sub-ranges outlined above.

FIGS. 4A through 4D show an example respiratory device of the respiratory system 10 having a main housing 100, which can implement the features described herein. The main housing 100 has a main housing upper chassis 102 and a main housing lower chassis 202. The main housing upper chassis 102 has a peripheral wall arrangement 106 (see FIG. 4C). The peripheral wall arrangement defines a humidifier or humidification chamber bay 108 for receipt of a removable humidification chamber 300. The removable humidification chamber 300 contains a suitable liquid such as water for humidifying gases that can be delivered to a patient.

In the form shown, the peripheral wall arrangement 106 of the main housing upper chassis 102 can include a substantially vertical left side outer wall 110 that is oriented in a front-to-rear direction of the main housing 100, a substantially vertical left side inner wall 112 that is oriented in a front-to-rear direction of the main housing 100, and an interconnecting wall 114 that extends between and interconnects the upper ends of the left side inner and outer walls 110, 112. The main housing upper chassis 102 can further include a substantially vertical right side outer wall 116 that is oriented in a front-to-rear direction of the main housing 100, a substantially vertical right side inner wall 118 that is oriented in a front-to-rear direction of the main housing 100, and an interconnecting wall 120 that extends between and interconnects the upper ends of the right side inner and outer walls 116, 118. The interconnecting walls 114, 120 are angled towards respective outer edges of the main housing 100, but can alternatively be substantially horizontal or inwardly angled.

The main housing upper chassis 102 can further include a substantially vertical rear outer wall 122. An upper part of the main housing upper chassis 102 can include a forwardly angled surface 124. The surface 124 can have a recess 126 for receipt of a display and user interface module 14. The display can be configured to display characteristics of sensed gas(es) in real time. An interconnecting wall 128 can extend between and interconnect the upper end of the rear outer wall 122 and the rear edge of the surface 124.

A substantially vertical wall portion 130 can extend downwardly from a front end of the surface 124. A substantially horizontal wall portion 132 can extend forwardly from a lower end of the wall portion 130 to form a ledge. A substantially vertical wall portion 134 can extend downwardly from a front end of the wall portion 132 and terminate at a substantially horizontal floor portion 136 of the humidification chamber bay 108. The left side inner wall 112, right side inner wall 118, wall portion 134, and floor portion 136 together can define the humidification chamber bay 108. The floor portion 136 of the humidification chamber bay 108 can have a recess 138 to receive a heater arrangement such as a heater plate assembly 140 or other suitable heating mechanisms for heating liquid in the humidification chamber 300 for use during a humidification process.

The main housing lower chassis 202 can be attachable to the upper chassis 102, either by suitable fasteners or integrated attachment features such as clips for example. The main housing lower chassis 202 can include a substantially vertical left side outer wall 210 that is oriented in a front-to-rear direction of the main housing 100 and is contiguous with the left side outer wall 110 of the upper chassis 102, and a substantially vertical right side outer wall 216 that is oriented in a front-to-rear direction of the main housing 100 and is contiguous with the right side outer wall 116 of the upper chassis 102. The main housing lower chassis 202 can further include a substantially vertical rear outer wall 222 that is contiguous with the rear outer wall 122 of the upper chassis 102.

The lower housing chassis 202 can have a lip 242 that is contiguous with the lip 142 of the upper housing chassis 102, and also forms part of the recess for receiving the handle portion 506 of the lever 500. The lower lip 242 can include a forwardly directed protrusion 243 that acts as a retainer for the handle portion 506 of the lever 500. Instead of the lever 500, the system can have a spring loaded guard to retainer the humidification chamber 300 in the humidification chamber bay 108.

An underside of the lower housing chassis 202 can include a bottom wall 230. Respective interconnecting walls 214, 220, 228 can extend between and interconnect the substantially vertical walls 210, 216, 222 and the bottom wall 230. The bottom wall 230 can include a grill 232 comprising a plurality of apertures to enable drainage of liquid in case of leakage from the humidification chamber 300 (for example from spills). The bottom wall 230 additionally can include elongated forward-rearward oriented slots 234. The slots 234 can additionally enable drainage of liquid in case of leakage from the humidification chamber 300, without the liquid entering the electronics housing. In the illustrated configuration, the slots 234 can be wide and elongate relative to the apertures of the grill 232 to maximize the drainage of liquid.

The lower chassis 202 can have a motor recess 250 for receipt of a motor and/or sensor module. The motor and/or sensor module may be non-removable from the main housing 100. The motor and/or sensor module can be removable or not removable from the main housing 100 (not shown). All of the walls and the ceiling 262 can be continuous, gas impermeable, and unbroken other than the gases flow passage. Therefore, the entire motor recess 250 can be gas impermeable and unbroken, other than the gases flow passage.

The motor and/or sensor module can be insertable into the recess 250 and attachable to the lower chassis 202. Upon insertion of the motor and/or sensor module into the lower chassis 202, the gases flow passage tube 264 can extend through the downward extension tube 133 and be sealed by the soft seal.

The humidification chamber 300 can be fluidly coupled to the apparatus 10 in a linear slide-on motion in a rearward direction of the humidification chamber 300 into the chamber bay 108, from a position at the front of the housing 100 in a direction toward the rear of the housing 100. A gases outlet port 322 can be in fluid communication with the motor.

The humidification chamber gases inlet port 306 can be complementary with the gases outlet port 322, and the humidification chamber gases outlet port 308 can be complementary with the gases inlet port 340. The axes of those ports can be parallel to each other to enable the humidification chamber 300 to be inserted into the chamber bay 108 in a linear movement. The respiratory device can have air and oxygen (or alternative auxiliary gas) inlets in fluid communication with the motor to enable the motor to deliver air, oxygen (or alternative auxiliary gas), or a mixture thereof to the humidification chamber 300 and thereby to the patient.

Figure 4D:
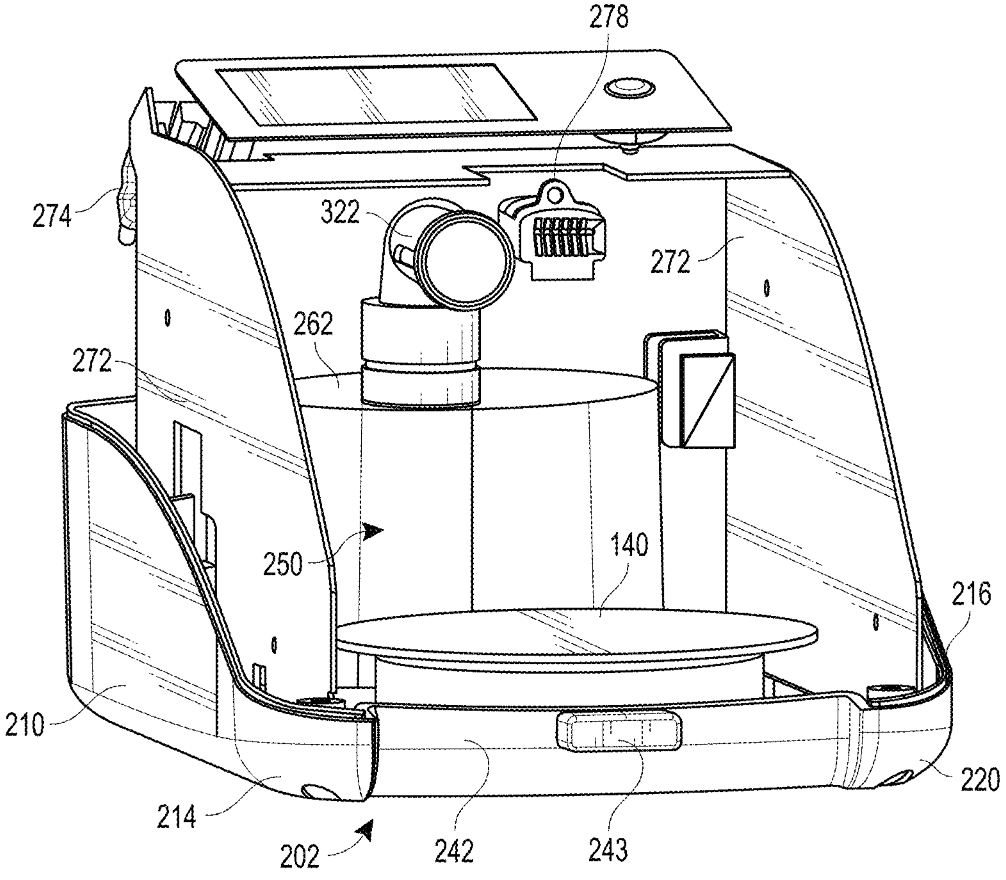
FIG. 4D is a front left side perspective view of the lower chassis of the main housing showing a heater plate assembly and other internal components.

As shown in FIG. 4D, the lower housing chassis 202 can include suitable electronics boards 272, such as sensing circuit boards. The electronics boards can be positioned adjacent respective outer side walls 210, 216 of the lower housing chassis 202. The electronics boards 272 can contain, or can be in electrical communication with, suitable electrical or electronics components, such as but not limited to microprocessors, capacitors, resistors, diodes, operational amplifiers, comparators, and switches. Sensors can be used with the electronic boards 272. Components of the electronics boards 272 (such as but not limited to one or more microprocessors) can act as the controller 13 of the apparatus.

One or both of the electronics boards 272 can be in electrical communication with the electrical components of the apparatus 10, including the display unit and user interface 14, motor, valve and the heater plate assembly 140, to operate the motor to provide the desired flow rate of gases, operate the humidification chamber 12 to humidify and heat the gases flow to an appropriate level, and supply appropriate quantities of oxygen (or quantities of an alternative auxiliary gas) to the gases flow.

The electronics boards 272 can be in electrical communication with a connector arrangement 274 projecting from the rear wall 122 of the upper housing chassis 102. The connector arrangement 274 may be coupled to an alarm, pulse oximetry port, and/or other suitable accessories. The electronics boards 272 can also be in electrical communication with an electrical connector 276 that can also be provided in the rear wall 122 of the upper housing chassis 102 to provide mains or battery power to the components of the device.

As mentioned above, operation sensors, such as flow, temperature, humidity, and/or pressure sensors can be placed in various locations in the respiratory device, the inspiratory conduit 16, and/or cannula 17. The electronics boards 272 can be in electrical communication with those sensors. Output from the sensors can be received by the controller 13, to assist the controller 13 to operate the respiratory system 10 in a manner that provides optimal therapy, including meeting inspiratory demand when the system is a high flow therapy system.

As outlined above, the electronics boards 272 and other electrical and electronic components can be pneumatically isolated from the gases flow path to improve safety. The sealing also prevents water ingress.

II. Example Heater Plate Assembly

FIGS. 5A through 5D depict cross-section views of example heater plate assemblies 540, 541, 542, 543. Each of the heater plate assemblies 540, 541, 542, 543 are example implementations of the heater plate assemblies described above, for example, the heater plate assemblies in the respiratory systems of FIGS. 1A-4D. As such, the heater plate assemblies 540, 541, 542, 543 can be implemented in any respiratory therapy device, examples of which are described above.

Figure 5A:
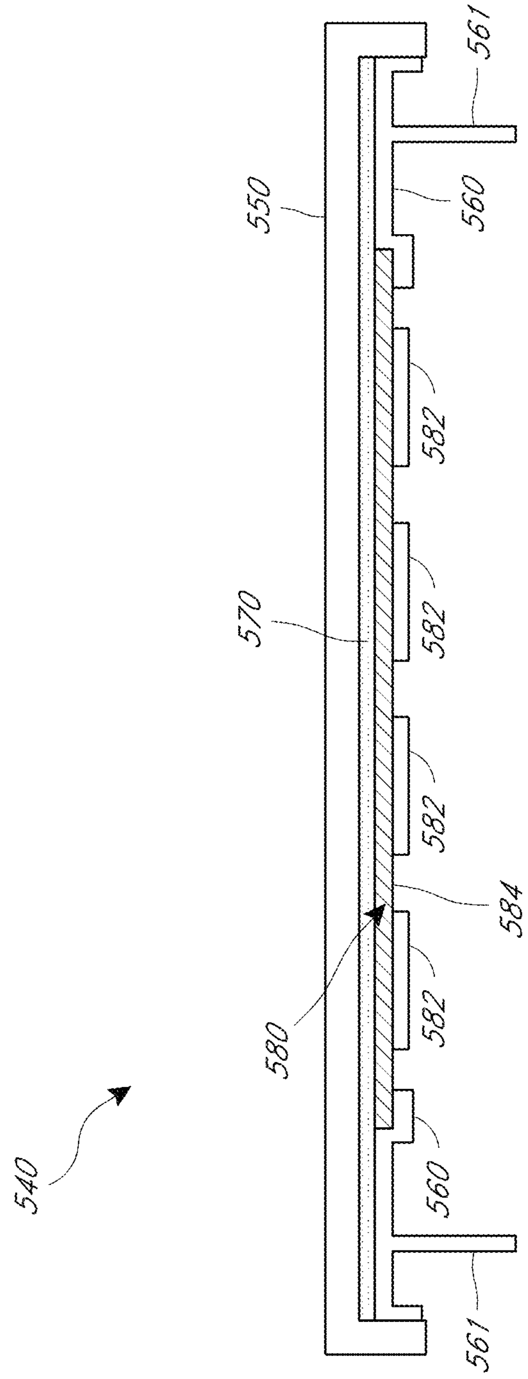
FIGS. 5A, 5B, 5C, and 5D are cross-section views of different example heater plate assemblies.

As shown in FIG. 5A, the example heater plate assembly 540 includes a heating plate 550, shroud 560, intermediate layer 570, and heating element 580. The heating plate 550 can be made of metal, such as aluminum or brass. When the heater plate assembly 540 is installed in a main housing, including in any of the devices described above, the heating plate 550 is brought into contact with a removable humidification chamber, examples of which are described above (for example, the removable humidification chamber 300).

The intermediate layer 570 can be located between the heating element 580 and the heating plate 550. The intermediate layer 570 can be an adhesive layer configured to affix the heating element 580 to the heating plate 550. Optionally, the adhesive layer can be a tape, a glue (optionally silicone based or epoxy based), or a thermally conductive pad (for example, Sil-Pad 2000™), or combinations of the same (for example, tape with a glue adhesive). Example glues include polyurethane, cyanoacrylate, silicone, epoxy resin, acrylics, hot melt (for example, ethylene vinyl acetate, polyamide, and polyolefin), elastomers, combinations of the same, and the like. When glue is used as the intermediate layer 570, the glue may be a one-part glue, a two-part glue (for example, a glue that mixes from two separate substances), or a more than two-part glue (for example, three-part). A two-part adhesive, for example, can be beneficial in that a two-part adhesive does not set until the two substances are mixed. Example tapes include KAPTON™ tape available from DUPONT™ or an acrylic tape. Further, the intermediate layer 570 need not be adhesive. Instead, the heating element 580 can be mechanically retained in contact with the heating plate 550 by the shroud 560 or by a cover (see, for example, FIG. 5C).

The intermediate layer 570 can also optionally be a dielectric, so as to insulate the heating plate 550 from the electrical current flowing through the one or more conductors 582. The immediate layer 570 can have a dielectric strength of about 1 kV/mm to about 100 kV/mm, or about 2 kV/mm to about 60 kV/mm, or about 7 kV/mm to about 40 kV/mm, or about 10 kV/mm to about 25 kV/mm, or about 15 kV/mm to about 20 kV/mm, or about 6 kV/mm, or about 12 kV/mm, or about 18 kV/mm, or about 24 kV/mm, or about 30 kV/mm, or about 36 kV/mm, or about 42 kV/mm, or about 48 kV/mm, or about 54 kV/mm, or about 60 kV/mm, or about 66 kV/mm, or about 72 kV/mm, or about 78 kV/mm, or about 84 kV/mm, or about 90 kV/mm, or about 96 kV/mm, or about 102 kV/mm. Further, in some configurations, the heater plate assembly may not include an intermediate layer 570 and the heating element 580 can be in direct contact with the heating plate 550.

The heating element 580 can include one or more conductors 582 attached to a substrate 584. The one or more conductors 582 can be or include resistive elements that produce heat when a current is applied to them. This heat can be transferred through the intermediate layer 570 to the heating plate 550 so as to heat the removable humidification chamber (not shown). The one or more conductors 582 can be a track or pads, among other configurations, examples of which are described in greater detail below. The one or more conductors 582 can be printed onto the substrate 584 (for example, as a thick film) or etched into the substrate 584. The substrate 584 can be a ceramic material, an aluminum oxide ceramic substrate, or any other suitable material, such as a thermally conductive material or a material that can withstand heat. The substrate can be included in a printed circuit board (PCB). The substrate 584 can also be a board of a PCB, a mica substrate, a KAPTON™ substrate, a fiberglass substrate, or a plastic substrate (for example a silicone substrate), combinations of the same, or the like. Different types of heating elements 580 can also optionally be used, such as a wire wound heater, etched foil heater, a heater coil, or a flexible PCB heater.

The intermediate layer 570 may hold the heating element in place and/or provide an interface for heat transfer. The immediate layer 570 can have thermal conductivity of about 0.1 W/mK to about 1.1 W/mK, or about 0.15 W/mK to about 7.5 W/mK, or about 0.2 W/mK to about 5 W/mK, or about 0.3 W/mK to about 3 W/mK, or about 0.5 W/mK to about 2 W/mK, or about 0.7 W/mK to about 1.5 W/mK, or about 0.8 W/mK to about 1.25 W/mK, or about 0.9 W/mK to about 1.1 W/mK, or about 0.1 W/mK, or about 0.2 W/mK, or about 0.3 W/mK, or about 0.4 W/mK, or about 0.5 W/mK, or about 0.6 W/mK, or about 0.7 W/mK, or about 0.8 W/mK, or about 0.9 W/mK, or about 1.0 W/mK, or about 1.1 W/mK. The intermediate layer 570 chosen may also have flame resistance. The intermediate layer 570 may have a useful temperature range of about −45° C. to about 200° C., or some other useful range, which is above the maximum operating temperature of the heater plate assembly. Optionally the layer 570 may have a useful temperature range of between about 0° C. to about 180° C., or between about 0° C. and about 150° C., or between about 10° C. and about 150° C., or between 10° C. and about 130° C., or about 10° C. and about 110° C.

The intermediate layer 570 may or may not be a continuous layer between the heating plate 550 and the heating element 580. Generally speaking, the intermediate layer 570 may have sufficient characteristics (for example, thickness, electrical resistance, etc.) to meet electrical insulation requirements in some or all jurisdictions. The intermediate layer 570 may be continuous or a substantially continuous intermediate layer 570. The layer 570 may be in the range of about 0.01 mm to about 5 mm thick, or about 0.1 mm to about 2 mm thick, or about 0.5 mm to about 2 mm thick, or about 0.1 mm thick, or about 0.2 mm thick, or about 0.25 mm thick, or about 0.4 mm thick, or about 0.5 mm thick, or about 0.8 mm thick, or about 1 mm thick, or about 1.2 mm thick, or about 1.4 mm thick, or about 1.5 mm thick, or about 1.6 mm thick, or about 2 mm thick, or about 3 mm thick.

The shroud 560 can be a plastic or glass member that can connect to the heating plate 550 optionally via the intermediate layer 570. Further, the shroud 560 can abut the heating element 580. For example, the shroud 560 may comprise a recessed region to retain and locate the heating element 580. The shroud 560 can locate and retain the heating element 580 relative to the heating plate 550. The shroud 560 can act to mechanically couple the heater plate assembly 540 to the main housing of the humidification system. To that end, the shroud can include legs 561 that can snap into or otherwise connect to the main housing. The leg 561 may include a protrusion (see FIGS. 7A, 9A, and 10A) to form a clip. The protrusion may face radially inwardly or outwardly. Examples of the shroud 560 are described in greater detail below.

Figure 5B:
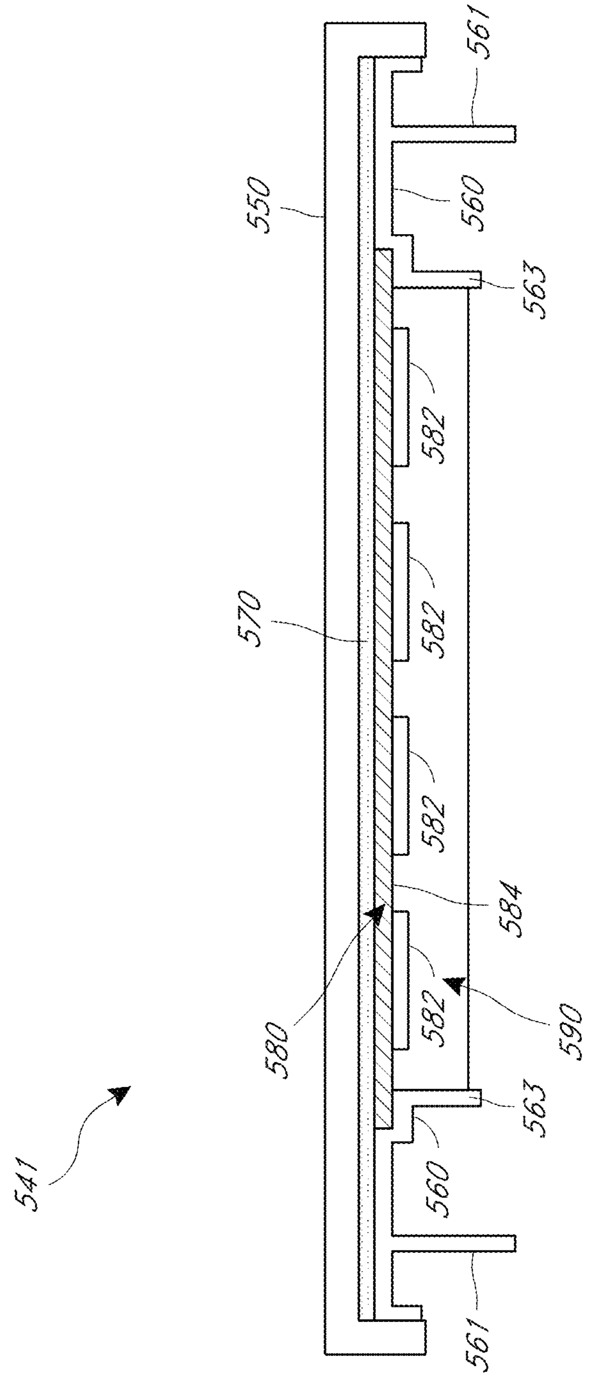

Turning to FIG. 5B, the heater plate assembly 541 is shown. The heater plate assembly 541 may include any of the features of the heater plate assembly 540 of FIG. 5A. However, the heater plate assembly 541 includes a few additional features. Specifically, the shroud 560 of the heater plate assembly 541 includes walls 563 (see element 762 of FIG. 8C for an example three-dimensional representation). The walls 563 can hold potting 590, which can protect the electronics, such as the conductors 582, from shock, vibration, moisture, corrosive agents, and the like. The potting 590 can be a material that covers the heating element 580 so as to protect the heating element 580. The potting 590 can be any suitable material, such as silicone resin, polyurethane potting, plastic overmoulding, epoxy potting, liquid silicone elastomers, combinations of the same, or the like.

Figure 5C:
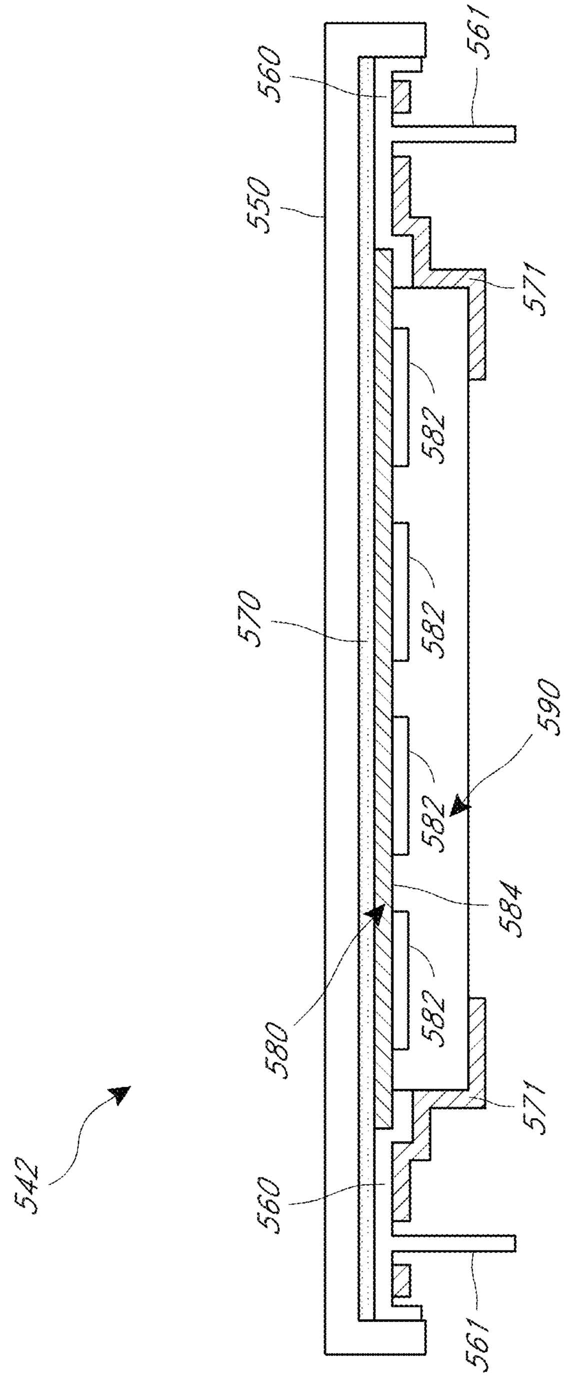

Turning to FIG. 5C, the heater plate assembly 542 is shown. The heater plate assembly 542 may include any of the features of the heater plate assembly 540 of FIG. 5A. The heater plate assembly 542 can include a few additional features. For example, the heater plate assembly 542 includes the potting 590, which may be any suitable potting material (examples described above). A potting cover 571 is applied to the shroud 560 and the potting 590. An example three-dimensional representation of the potting cover 571 is described below with respect to FIG. 7C.

Figure 5D:
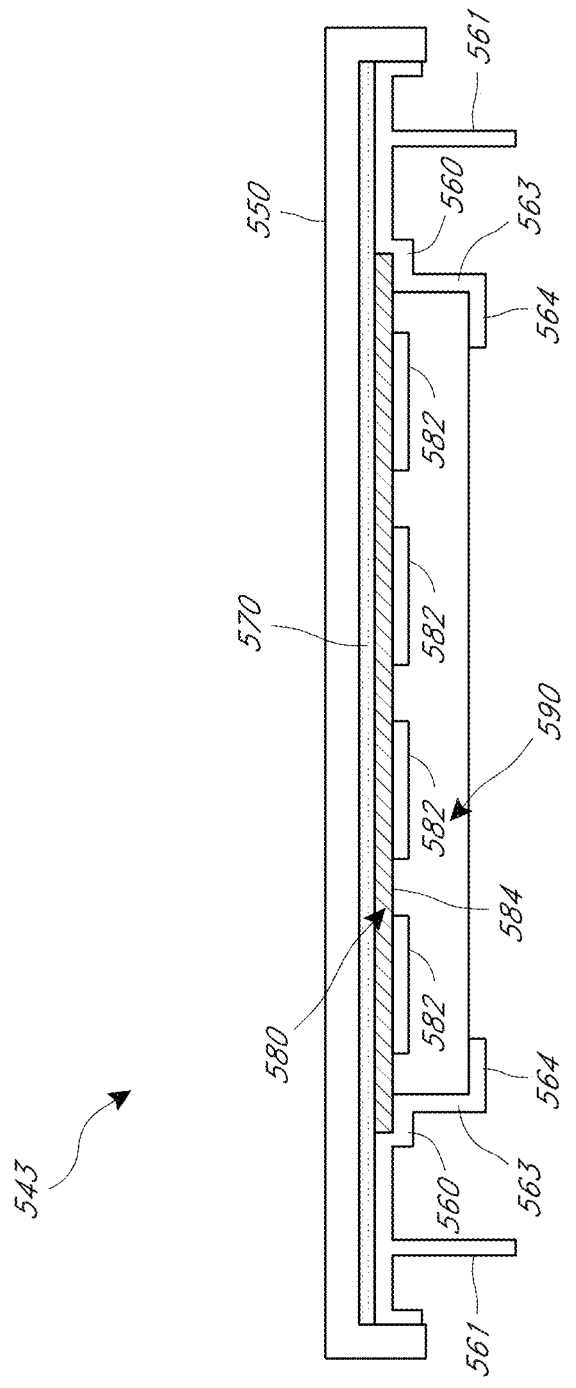

Turning to FIG. 5D, the heater plate assembly 543 is shown. The heater plate assembly 543 may include any of the features of the heater plate assembly 541 of FIG. 5B. However, the heater plate assembly 543 includes a few additional features. Specifically, the shroud 560 of the heater plate assembly 543 includes walls 563 and a lip 564 extending generally perpendicularly from the walls 563. The lip 564 can prevent the potting from falling out. The walls 563 and the lips 564 can function similar to the potting cover 571 of FIG. 5C. In this configuration, a potting cover may not be required.

Figure 6:
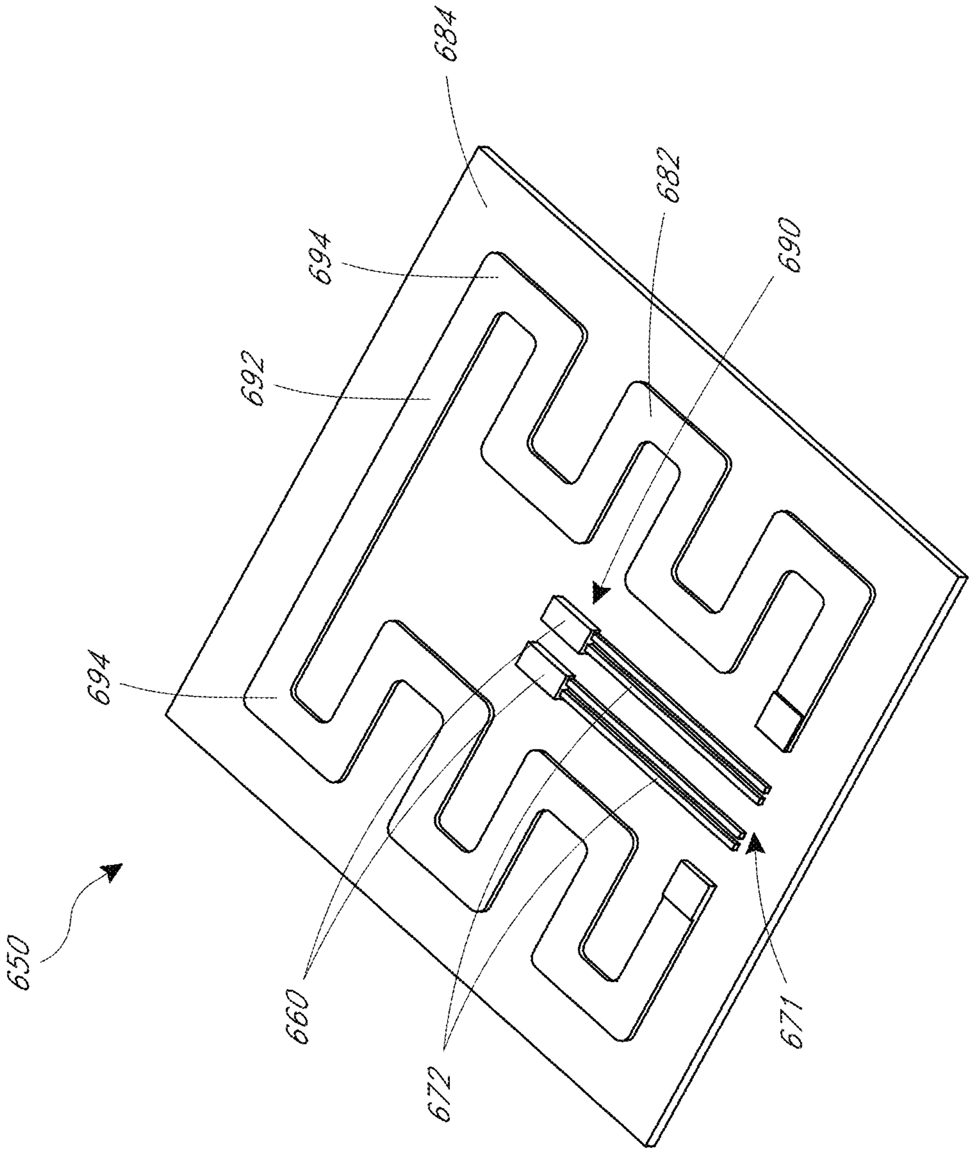
FIG. 6 is a top view of an example heating element with a single resistive track.
Figure 10B:
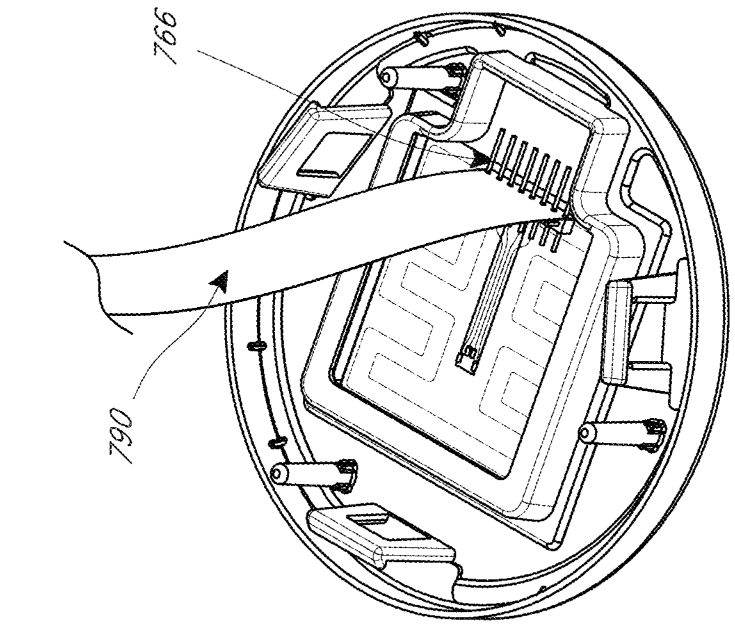
FIG. 10B illustrates a partial bottom view of the example heater plate assembly of FIG. 10A connected to a flexible PCB.
Figure 10A:
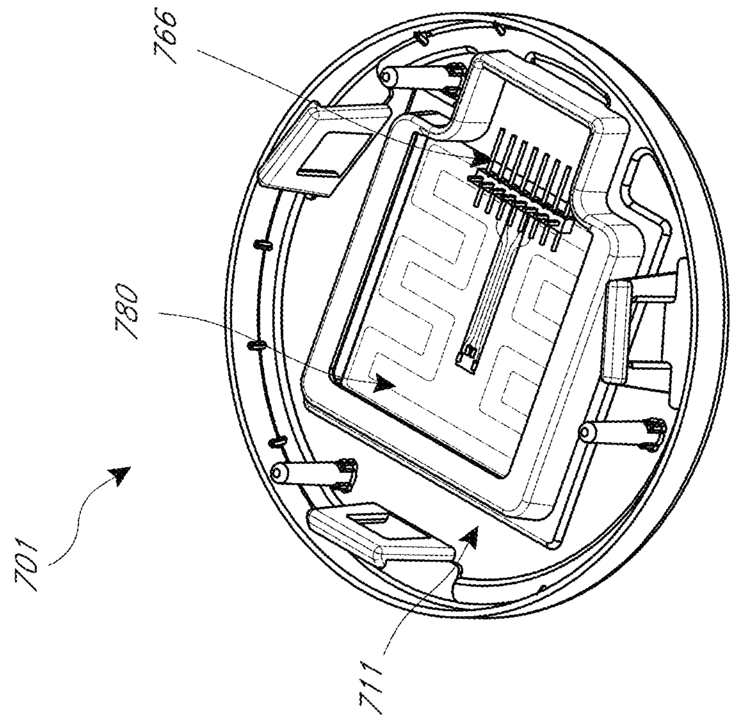
FIG. 10A illustrates a bottom view of an example heater plate assembly.

FIG. 6 is a top view of an example heating element 650 (see also heating element 780 of FIG. 10A). The heating element 650 is an example of the heating element 580 described above. The heating element 650 includes a conductor 682 on a substrate 684. Temperature sensors 660 are also disposed on the substrate. The temperature sensors 660 can be thermistors or any other type of suitable temperature sensor. Although two temperature sensors 660 are shown, fewer or more sensors 660 may be included.

In FIG. 6, the conductor 682 is a resistive track 682. The conductor 682 can be a single resistive track 682, as opposed to multiple parallel tracks. Multiple parallel resistive tracks (also referred to herein as a "multi-track arrangement") may also optionally be used.

The resistive track 682 has been arranged to provide for a central region 690 of the heating element 650 that is further from any part of the resistive track 682 than other portions of the heating element 650. This central region 690 can be used for the temperature sensors 660, which may give incorrect measurements if the temperature sensors 660 are located too close to the resistive track 682.

The temperature sensors 660 can be spaced from the resistive track 682. A spacing between the temperature sensors 660 and the resistive track 682 can be greater than spacing between portions of the resistive track 682. A spacing between the temperature sensors 660 and the resistive track 682 can be about 1 cm to about 20 cm, or about 2 cm to about 15 cm, or about 5 cm to about 10 cm, or about 6 cm to about 7 cm.

The resistive track 682 can be wound in turns on the substrate 684, except that the resistive track 682 may not disposed in the central region 690 of the substrate 684. The resistive track 682 can also feature a single path.

An advantage of having a single path (as opposed to multiple paths in parallel) is the added safety if a segment 692 of the resistive track 682 were to become damaged. If a segment 692 of the resistive track 682 were to become damaged, the circuit would be broken and the heating element 650 would no longer function. If a segment were to become damaged in a multi-track arrangement, an increased current and power may be delivered to the remaining unbroken paths. This may result in uneven heat distribution and the formation of hot spots that could cause stress and cracking of the heating element 650 and heating plate. Additionally, the resulting current and power delivered to the remaining tracks in a multi-track arrangement may dangerously overload the hardware.

Additionally, conductors 672 that are in electrical communication with the temperature sensor 660, and the conductor 682, can terminate in an area 671 of the substrate 684 that can connect with wires or a flexible PCB (not shown). The wires or flexible PCBs can supply power to the conductors 682 and can sense signals from the temperature sensors 660 via the conductors 672. The area 671 can be proximate an end of the substrate 684. This grouping can allow for easier assembly and a tidier layout of the wires. Additionally, this grouping can leave the possibility for the wires to be replaced by a single flexible PCB (see FIGS. 10A-10C).

Figure 7A:
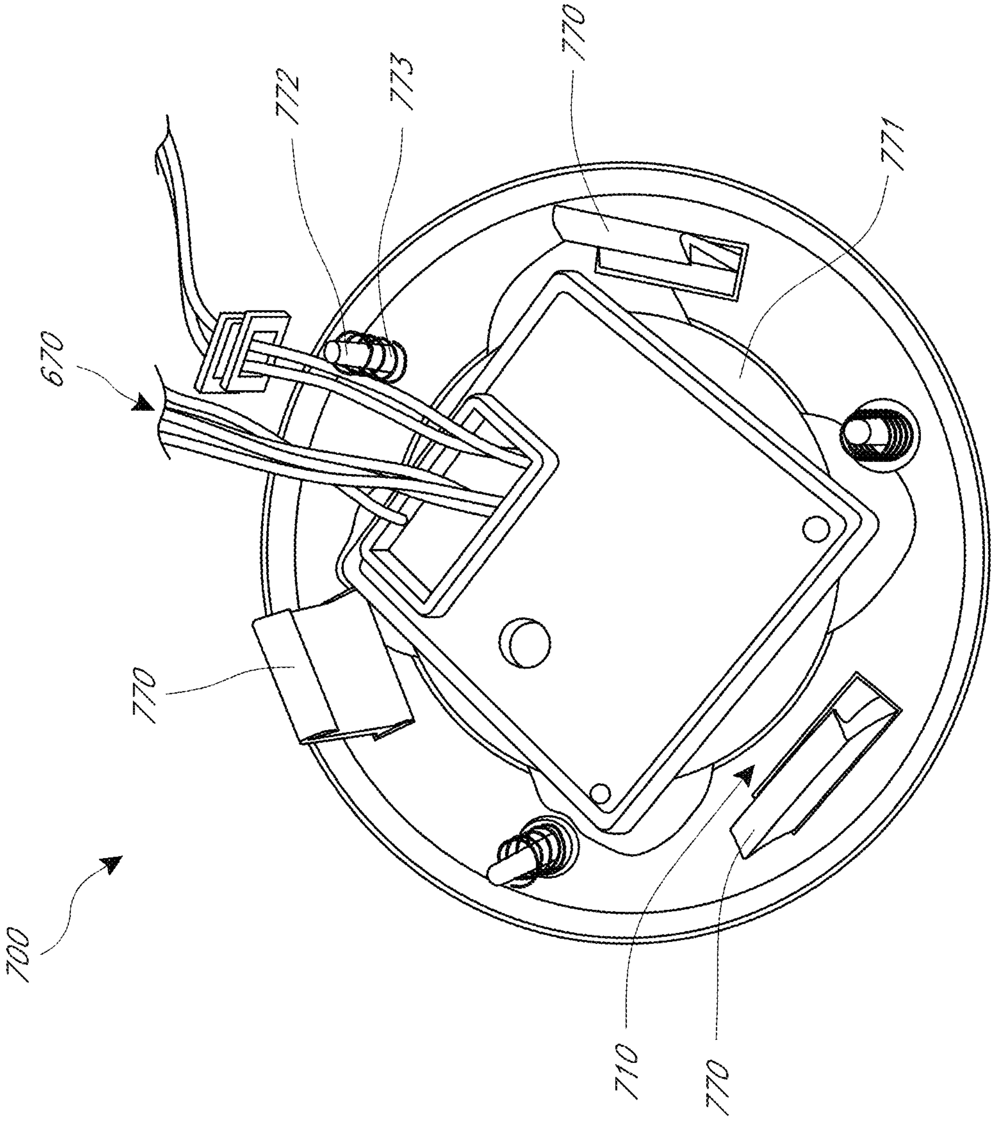
FIG. 7A is a bottom view of an example heater plate assembly.
Figure 8A:
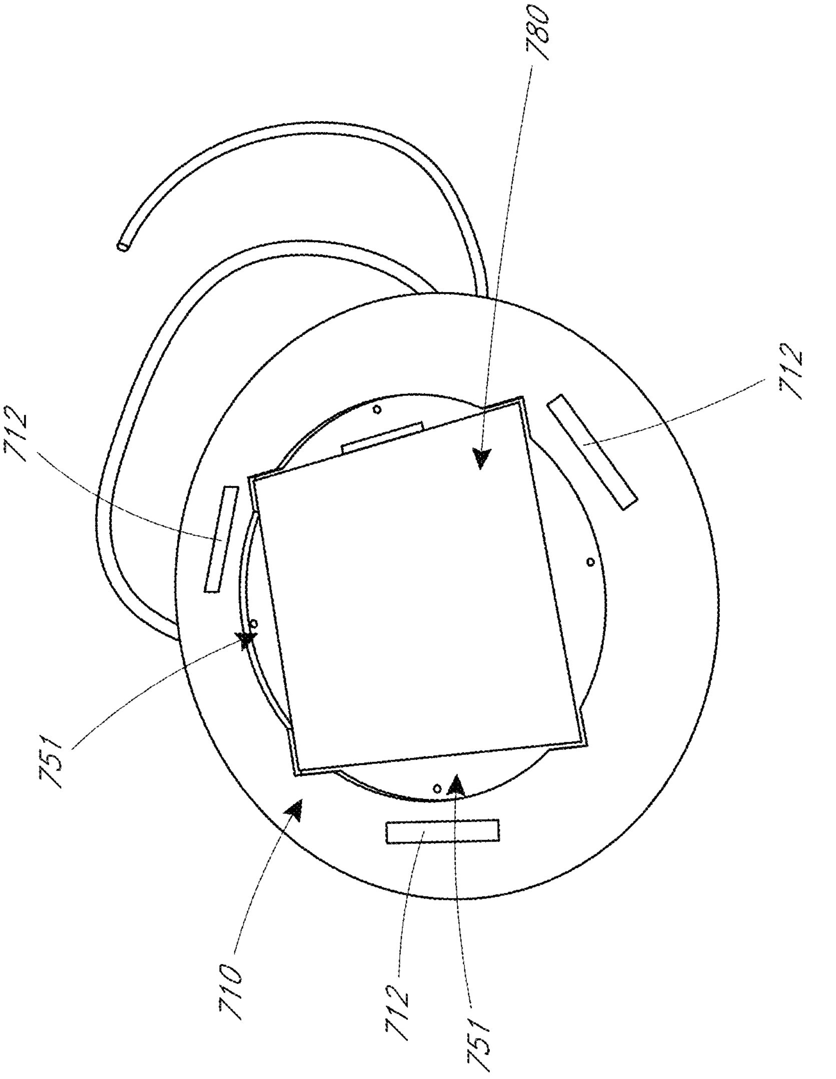
FIG. 8A is an example top view of the shroud of FIG. 7A together with an example heating element.
Figure 8C:
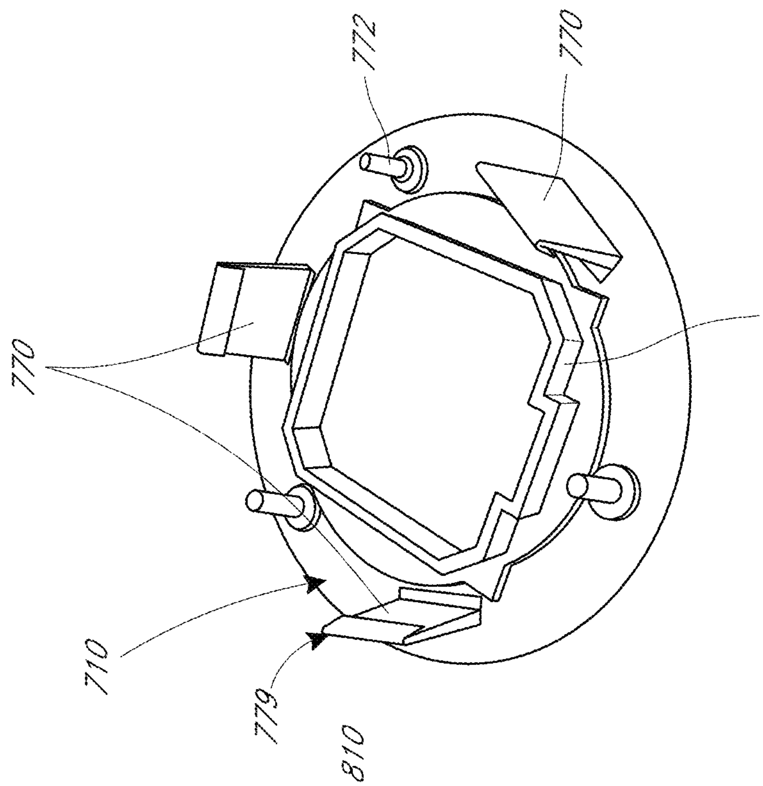
FIG. 8C depicts a bottom view of the example shroud of FIG. 7A.
Figure 8B:
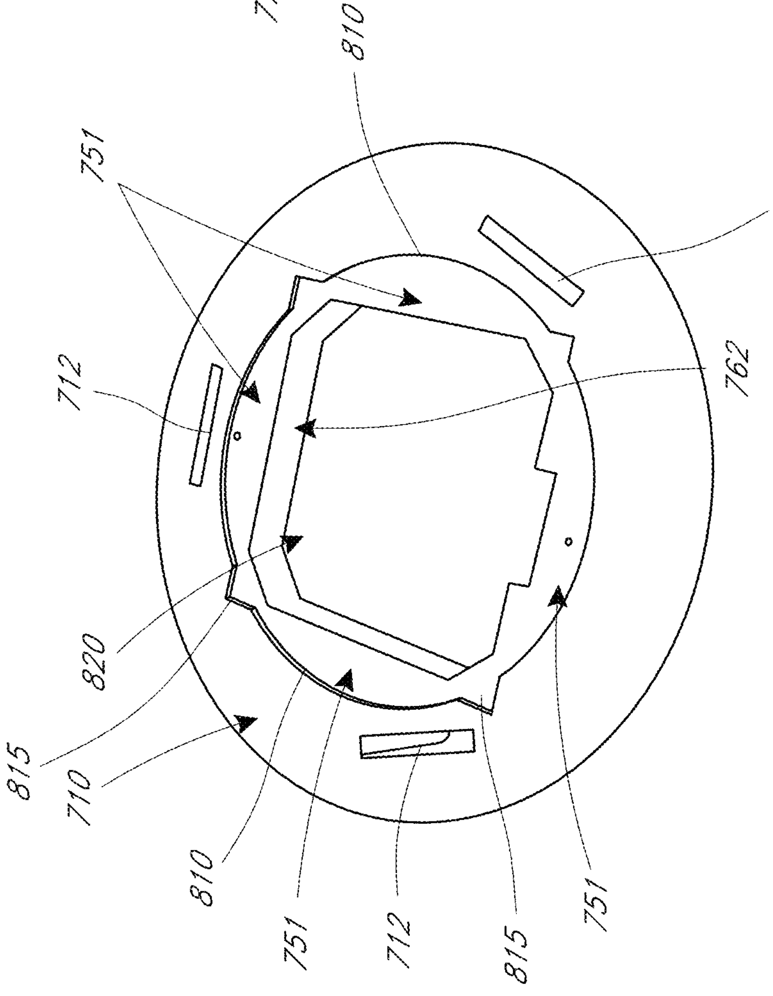
FIG. 8B depicts a top view of the example shroud of FIG. 7A.
Figure 9B:
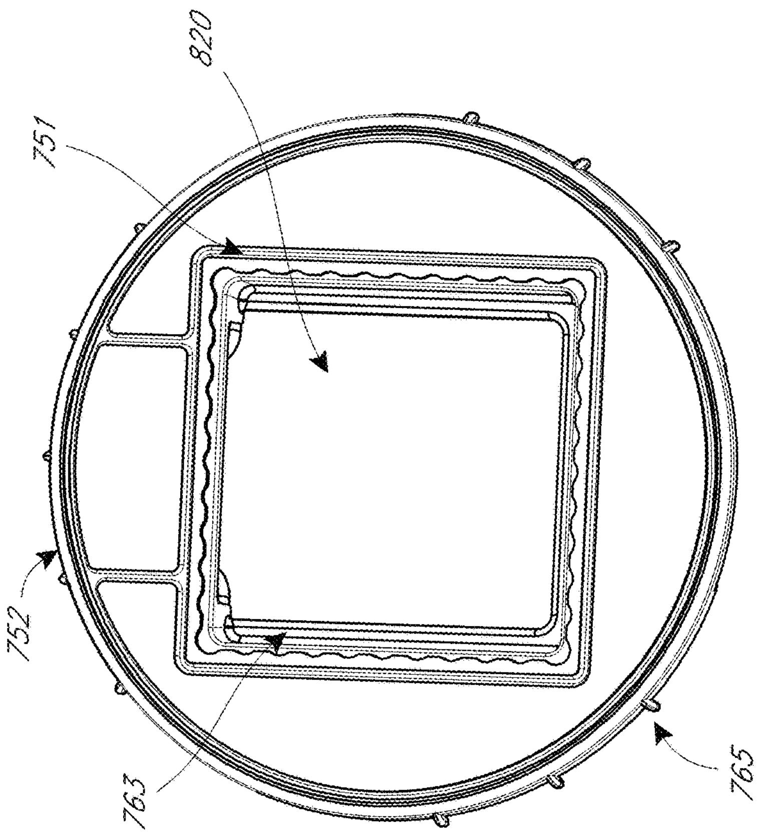
FIG. 9B illustrates a top view of the example shroud of FIG. 9A.
Figure 9A:
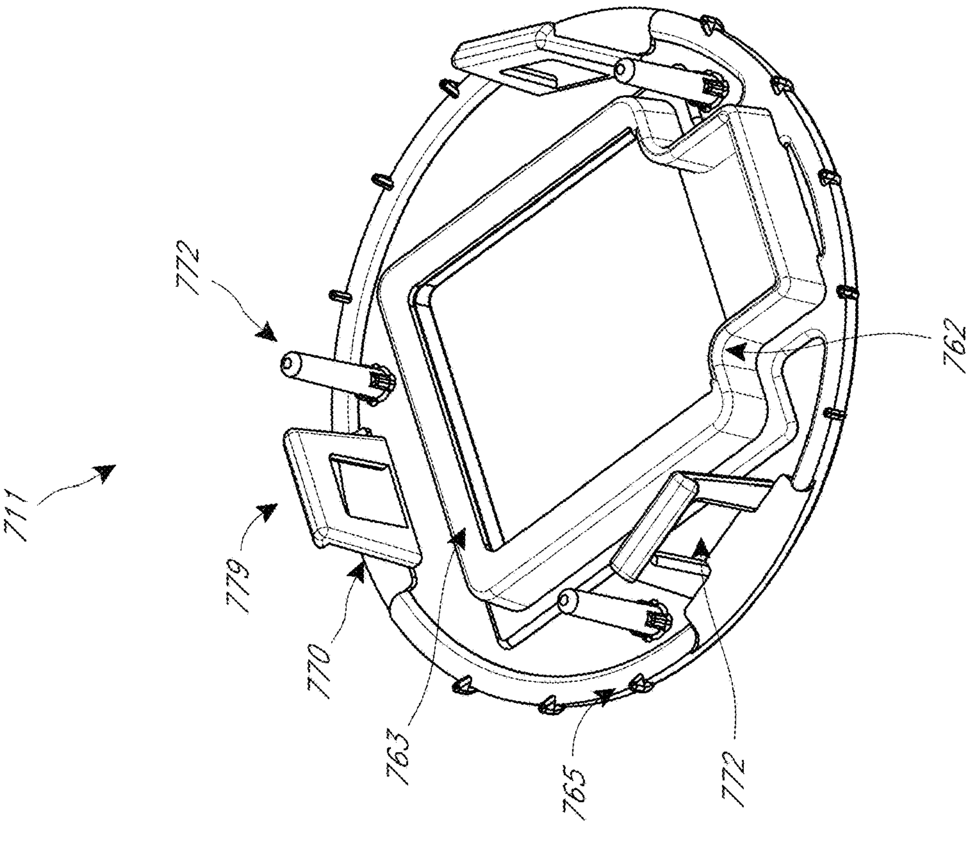
FIG. 9A illustrates a bottom view of another example shroud.
Figure 9C:
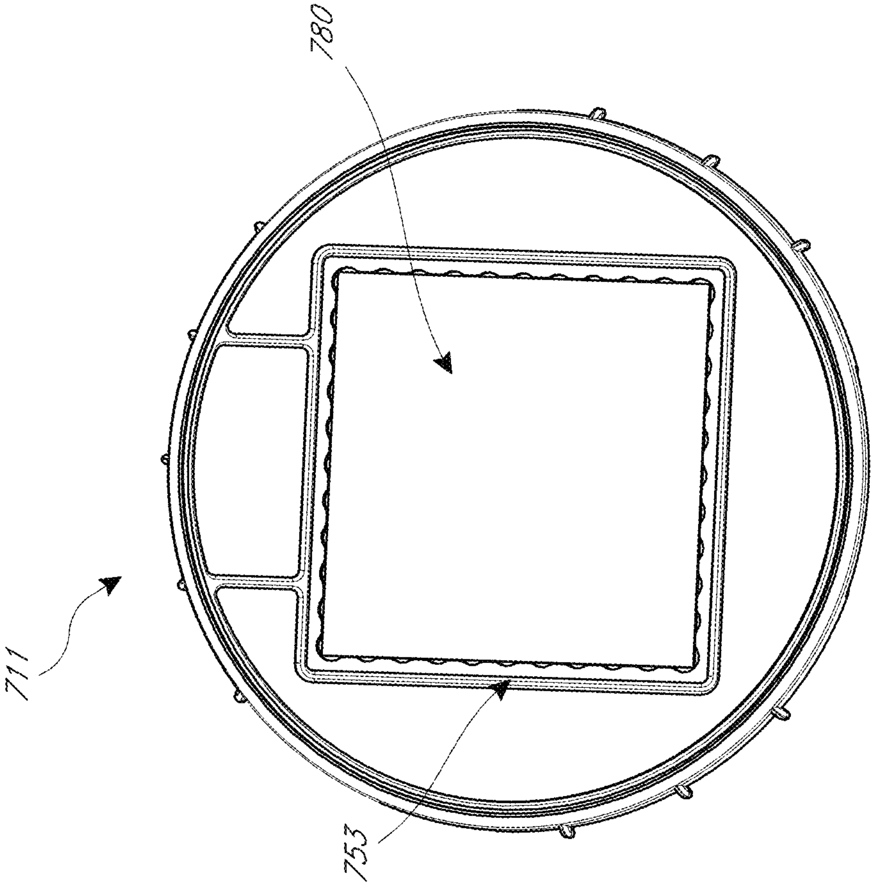
FIG. 9C illustrates a top view of the example shroud of FIG. 9A with an example heating element.

FIG. 7A is a bottom view of an example heater plate assembly 700 depicting an example potting 771 over a shroud 710 (partially shown). FIGS. 8A-8C depict fuller views of the shroud 710 apart from the heating plate. FIGS. 9A-9C depict fuller views of a shroud 711. FIGS. 10A-10B illustrate bottom views of an example heater plate assembly 701 incorporating the shroud 711. The shroud 710, 711 are examples of the shroud 560 of FIG. 5. Likewise, the heater plate 700, 701 are examples of the heater plate 550, and the heating element 780 is an example of the heating elements 580 and 650.

The shroud 710, 711 have been designed such that a cover may not be required for the heater plate assembly 500 (see FIGS. 5A, 5B). As shown in more detail in FIGS. 8A-8C and 9A-9C, the shroud may be a single part shroud 710, 711. The shroud may also be a multiple part shroud, for example a two part shroud. The shroud 710 may comprise pins 772 and walls 762 to enclose potting 771 (see FIGS. 5B, 7A, 8C). The pins 772 can hold springs 773 (FIG. 7A) in the main housing when the heater plate assembly 700 is connected to the main housing. The springs can provide an upwards force on the heater plate assembly 700 by pushing against the main housing. The springs can be compressed to lower the heater plate assembly 700 when the chamber is being inserted. The shroud 711 as shown in FIGS. 9A-9B can also include the pins 772 and walls 762. The walls 762 of the shroud 711 may be shorter or smaller than the walls 762 of the shroud 710. The walls 762 of the shroud 711 can also include a lip 763 that is generally perpendicular to the walls 762. The lip 763 can be similar to the lip 564 in FIG. 5D. The lip 763 can prevent the potting from falling out without requiring a separate potting cover, such as shown in FIG. 5C.

Figure 7B:
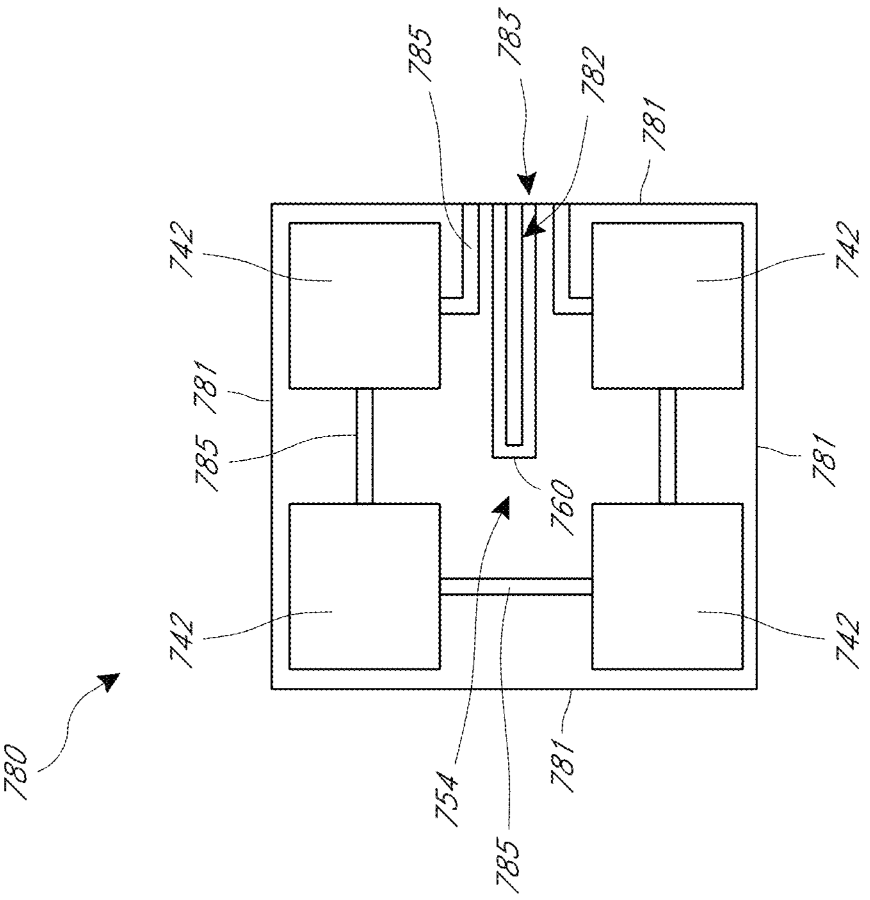
FIG. 7B is a top view of an example heating element with resistive pads.
Figure 7C:
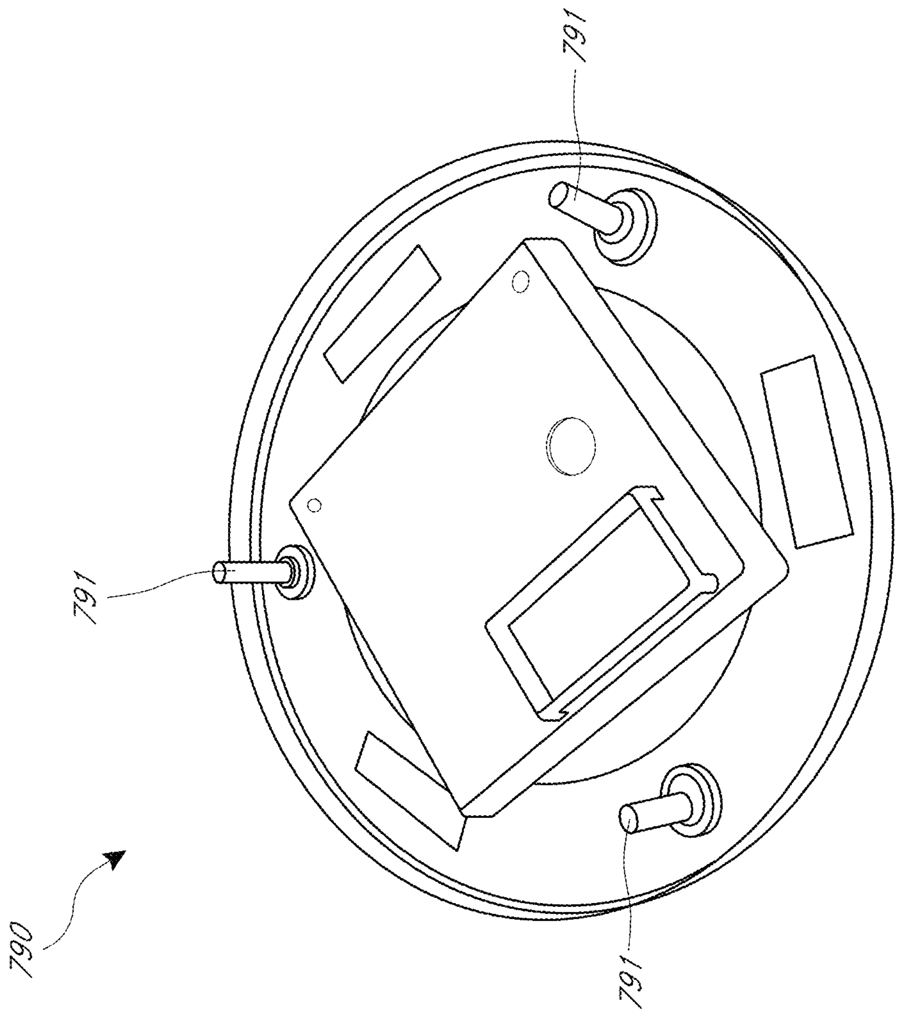
FIG. 7C is a top perspective view of an example cover for the heater plate assembly.

A cover can also be used together with or in place of the shroud 710, 711, such as the cover 790 shown in FIG. 7C. The cover 790 may be applied to the bottom of the heater plate assembly for further protection of the heater plate assembly. The cover 790 may be made of plastic or glass or some other suitable material. Legs 791 of the cover 790 can connect the heater plate assembly directly to the main housing such that the legs 561, 770 may be omitted from the shroud 560, 710, 711.

Referring again to FIGS. 7A, 8A-8C, 9A-9C and 10A, the walls 762 of the shroud 710, 711, and/or the cover 790 can hold the potting of the electrical connections of the heating element 780. The shroud 710 (or the shroud 710 and a cover 790) may also provide for a potting boundary (see, for example, FIGS. 5B and 5C). The walls 762 may act to constrain the potting material (for example while the potting material sets or cures). Optionally, the shroud 710 (or the shroud 710 and a cover 790) may have an overhanging portion configured to provide protection to the potting material and/or a potting boundary. As shown in FIGS. 9A-9B, the walls 762 of the shroud 711 can include an example of the overhanging portion, a lip 763 that is generally perpendicular to the walls 762. The lip 763 can be similar to the lip 564 in FIG. 5D. The lip 763 can prevent the potting from falling out without requiring a separate potting cover, such as shown in FIG. 5C. The overhanging portion may also include at least one opening to allow for the passage of wires 670 (for example as shown in FIG. 7A) or the flexible PCB (for example as shown in FIG. 10B). The overhanging portion may be continuous over the entire bottom surface of the potting material or may be discontinuous.

Alternatively, the heating element may be overmoulded to the heating plate (for example, the shroud and/or the intermediate layer described above may be omitted). The overmould may provide adhesion of the heating element to the heating plate, together with or in place of using the intermediate layer to adhere the heating element to the heating plate.

The shroud 710, 711 can include legs 770, which can act as clips which clip the heater plate assembly to the main housing in corresponding recesses (not shown). As shown in FIG. 8C, the protrusion 779 forming the clip can face radially inward. As shown in FIG. 9A, the protrusion 779 can face radially outward. The leg 770 of the shroud 711 can also include an opening 772, such as a cut-out section in the middle of the leg. The legs 770 may clip onto the main housing during assembly and be unable to be removed afterwards. This arrangement can be beneficial in preventing or reducing the chance of unwanted disassembly of the heater plate assembly. In order to remove the heater plate once assembled, at least one of the legs would have to be broken. However, the legs 770 may also be removed without damaging or breaking the components to facilitate maintenance and repair of the heater plate assembly. As shown in FIGS. 9A-9B, the shroud 711 can also include a plurality of ribs 765 along its outer edge. The ribs 765 can be press fit ribs. The ribs 765 can form an interference fit with the heating plate during assembly. This interference fit can further help to hold the heating plate and shroud 711 together, for example, during assembly prior to the curing of the adhesive, or after the curing of the adhesive to additionally secure the heating plate and the shroud 711 together.

Referring again to FIGS. 8A-8C in more detail, FIG. 8A depicts a top view of the shroud 710 with an installed heating element 780, while FIGS. 8B-8C depict both a top view (FIG. 8B) and bottom view (FIG. 8C) without an installed heating element 780. The shroud 710 can press up against the heating plate as described above. The example shroud 710 shown includes a region 751 in which the heating element 780 can sit. This region 751 can be recessed to allow adhesive to enter, when adhesive, such as glue is used as the intermediate layer 570 to adhere the heating element 780 and the shroud 710 to the heating plate, such as via the opening 820. This recessed region 751 can allow for an area where excess glue can be directed when the heating element 780 and the heating plate are squeezed together.

With reference to FIG. 8B, the recess 751 can include circular regions 810 and corner regions 815. The circular regions 810 have a partially circular shape, or curved shape, and thus may be considered as curved recesses. There can be four circular regions 810 and four corner regions 815. The recess 751 can have a substantially circular shape, defined by the circular regions 810, with the perimeter of the circular shape periodically interrupted with the corner regions 815. As can be seen in FIG. 8A, the corner regions 810 of FIG. 8B can permit the heating element 780 to be recessed into the shroud 710. When the heating element 780 is recessed into the shroud 710, the corners of the heating element 780 can mate or approximately mate with the corner regions 815 of the shroud 710. However, when the heating element 780 is recessed into the shroud 710, the circular regions 810 do not receive the heating element 780. Rather, the circular regions 810 can be adjacent to the heating element 780 (or the heating element 780 can overlap a small portion of the circular regions 810). Thus, at least some excess adhesive used to adhere the heating element 780 to the heating plate can be squeezed out from between the heating element 780 and the heating plate into the circular regions 810. The circular regions 810 may be considered relief channels, or collectively, a relief channel, for excess adhesive when the heating element 780 is pressed onto the shroud 710. There are four circular regions 810 or relief channels shown. Fewer than four or more than four relief channels may be provided, including as few as one relief channel. The relief channel need not be circular, but instead could be square, rectangular, or have any other suitable shape. The relief channel can be, for example, a hole or a series of holes in the shroud. One or more holes may be combined with the other relief channel examples described herein to form the relief channel.

The circular shape of the recess 751 can also be large enough in diameter that there are no corner regions 815; instead, the heating element 780 can fit within the perimeter of the circular shape. However, having the corner regions 815 can ensure or attempt to ensure that the heating element is placed in the correct orientation within the shroud 710.

Referring to FIGS. 9A-9C in more detail, FIG. 9C depicts a top view of the shroud 711 with an installed heating element 780, while FIGS. 9A-9B depict both a top view (FIG. 9B) and bottom view (FIG. 9A) without an installed heating element 780. The shroud 711 can press up against the heating plate as described above. An upper surface of the example shroud 711 shown includes a region 751 in which the heating element 780 can sit. This region 751 can be recessed to allow adhesive to enter, when adhesive, such as glue is used as the intermediate layer 570 to adhere the heating element 780 and the shroud 711 to the heating plate, such as via the opening 820. As shown in FIG. 9B, the upper surface of the shroud 711 can have a groove 752 that runs along a perimeter of the shroud 711. The region 751 also has an additional groove that runs along the edge of the region 751 for receiving the heater element. The groove 752 and the groove of the region 751 can be joined and can provide a cavity for receiving excess adhesive when the heating element 780 and the heating plate are squeezed together instead of spilling below the upper surface of the shroud 711.

The region 751 of the shroud 711 can also include an uneven surface. As shown in FIG. 9C, the uneven surface can create small intermittent gaps 753 between the heating element 780 and the edge of the region 751. These gaps 753 can also act as cavities for any excess adhesive.

The wires shown can be soldered to the heating element prior to coupling with the heating plate, which can be beneficial as the heating plate can act as a heat sink and may allow heat to dissipate during the soldering process. Therefore, it is preferable to solder the wires to the heating element prior to coupling with the heating plate. The wires could optionally be replaced by a flexible printed circuit board as described above. A flexible PCB can be beneficial in preventing wires from tangling and providing easier assembly. If a flexible PCB is used, such as shown in FIG. 10B, then the heating element can be designed with the electrical connection points being in close proximity. As shown in FIG. 10A, the heater plate assembly 701 can include a connector 766 attached to the heating element 780 (such as having any of features of the heating element 650 of FIG. 6). The wires or flexible PCB 790 (such as shown in FIG. 10B) can be soldered to the connecter 766 or connected using a reciprocating connector. This prevents or reduces damage to the heating element by the heat from the soldering process. Soldering directly to the heating element is inherently difficult due to the heat being sucked away from the solder joint as described above, particularly if the heating element is already coupled to the heating plate. To overcome this, the heating element may be pre-heated, or alternatively the soldering iron may be set to an excessively high temperature, both of which may damage the heating element. Having a pre-soldered connector on the element avoids this problem, as the heat would not dissipate as rapidly due to the low thermal conductivity of the connector. Additionally, the connector can be pre-soldered to the heating element using reflow soldering, which may not be applicable when connecting the flexible PCB or the wires.

Figure 10C:
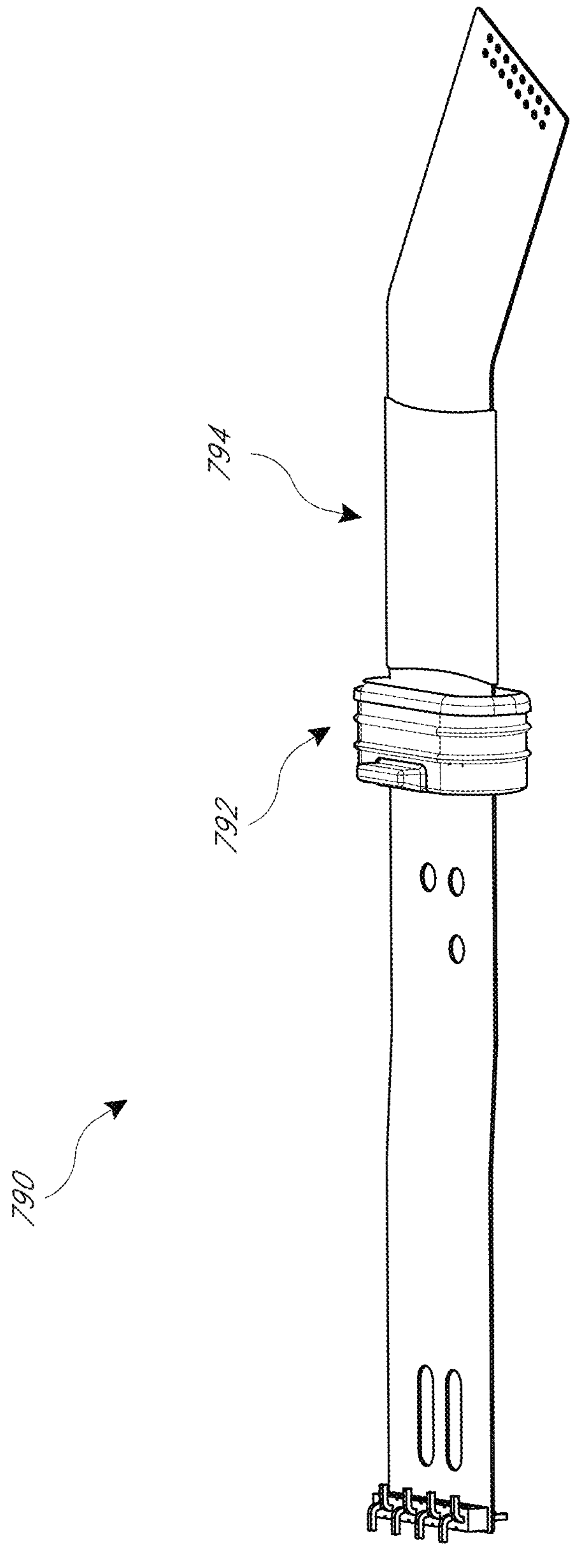
FIG. 10C illustrates an example flexible PCB.

As shown in FIG. 10C, the flexible PCB 790 can be provided with a sealing member 792. The sealing member 792 can form a seal with an aperture in the device housing. A section of the flexible PCB 790 can also have an insulating element 794 applied to the section. The insulating element 794 can increase the electrical insulation of the section of the flexible PCB 790 that may be in close proximity to the device's power board. The flexible PCB can also be manufactured with a thicker and/or wider cross section for at least the section that may be in close proximity to the device's power board.

The example heating element 780 shown can optionally include resistive pads instead of a resistive track. In FIG. 7B, an example arrangement of resistive pads 742 is shown. The heating element 780 can include 4 main resistive pads 742, which may be spaced out evenly, with a wider section down the middle 754 of the substrate 781. The wider section of the substrate 781 can receive, for example, temperature sensor (s) 760, with similar benefits as the central region 690 of FIG. 6. The resistive pads 742 in this example are disposed on a substrate 781 and are connected in series by conductors 785. The resistive pads 742 may provide for a more even distribution of heat compared to a series of tracks which may generate localized hot spots.

As described above, a central region 754 is formed in the middle of the resistive pads 742, where a temperature sensor 760 is disposed. The conductors 785 for the resistive pads 742 and conductors 782 attached to the temperature sensor 760 can terminate in a region 783 that groups these conductors together, so that a set of wires or one or more flexible PCBs could be attached thereto.

Instead of the track or resistive pads described herein, other configurations of resistive heating elements may be provided in other examples.

III. Example Control System

The following example control system and circuits can be implemented with any of the devices described above.

Figure 11A:
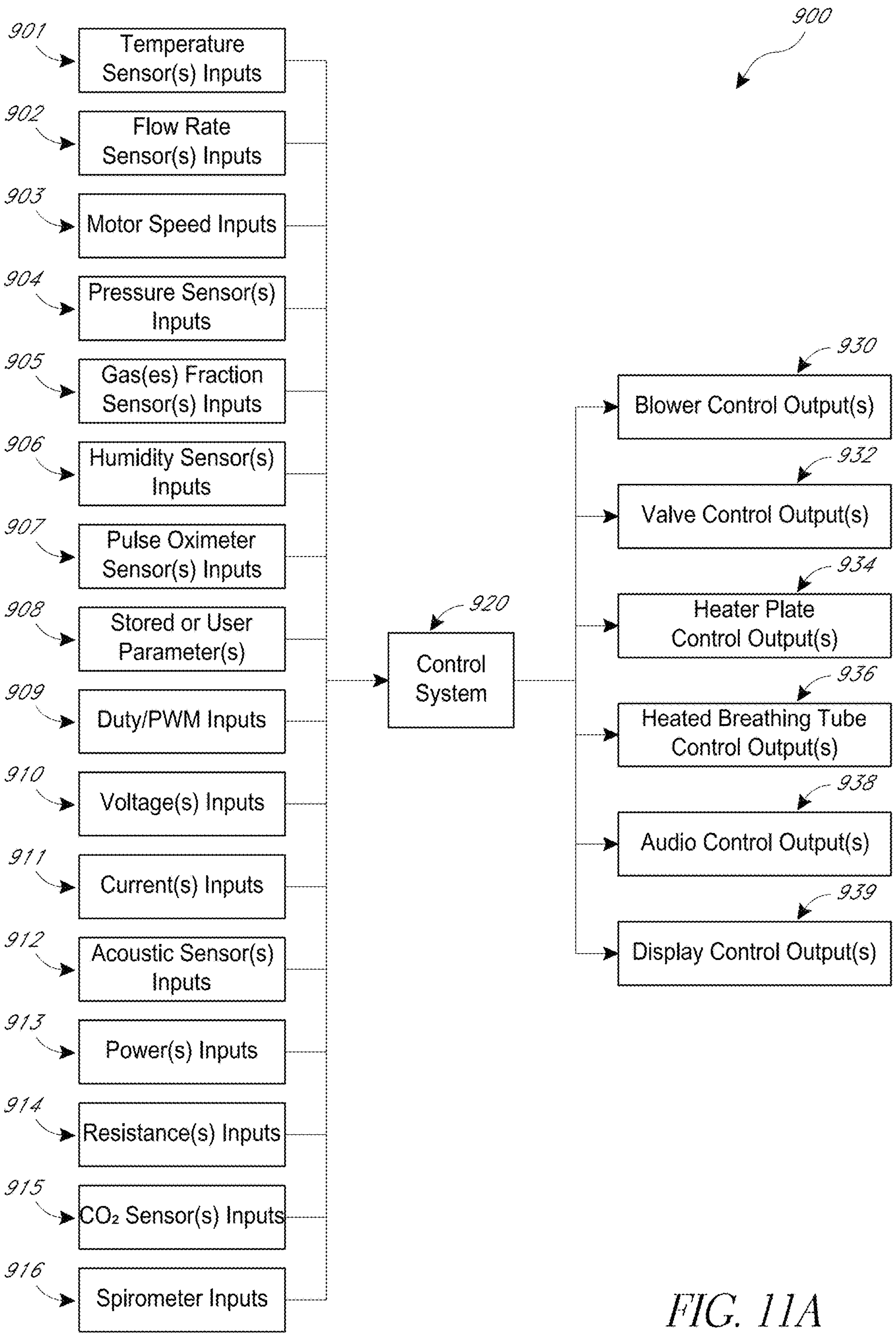
FIG. 11A illustrates a block diagram of a control system interacting with and/or providing control and direction to components of a respiratory system.

FIG. 11A illustrates a block diagram 900 of an example control system 920 that can detect patient conditions and control operation of the respiratory system including the gas source. The control system 920 can manage a flow rate of the gas flowing through the respiratory system as it is delivered to a patient. For example, the control system 920 can increase or decrease the flow rate by controlling an output of a motor speed of the blower unit (hereinafter also referred to as a "blower motor") 930 or an output of a valve 932 in a blender. The control system 920 can automatically determine a set value or a personalized value of the flow rate for a particular patient as discussed below. The flow rate can be adjusted or attempted to be optimized by the control system 920 to improve patient comfort and therapy.

The control system 920 can also generate audio and/or display/visual outputs 938, 939. For example, the flow therapy apparatus can include a display and/or a speaker. The display can indicate to the physicians any warnings or alarms generated by the control system 920. The display can also indicate control parameters that can be adjusted by the physicians. For example, the control system 920 can automatically recommend a flow rate for a particular patient. The control system 920 can also determine a respiratory state of the patient, including but not limited to generating a respiratory rate of the patient, and send it to the display, which will be described in greater detail below.

The control system 920 can change heater control outputs to control one or more of the heating elements (for example, to maintain a temperature set point of the gas delivered to the patient). The control system 920 can also change the operation or duty cycle of the heating elements. The heater control outputs can include heater plate assembly control output(s) 934 and heated breathing tube control output(s) 936.

The control system 920 can determine the outputs 930-939 based on one or more received inputs 901-916. The inputs 901-916 can correspond to sensor measurements received automatically by the controller 600 (shown in FIG. 11). The control system 920 can receive sensor inputs including but not limited to temperature sensor(s) inputs 901, flow rate sensor(s) inputs 902, motor speed inputs 903, pressure sensor(s) inputs 904, gas(s) fraction sensor(s) inputs 905, humidity sensor(s) inputs 906, pulse oximeter (for example, SpO2) sensor(s) inputs 907, stored or user parameter(s) 908, duty cycle or pulse width modulation (PWM) inputs 909, voltage(s) inputs 910, current(s) inputs 911, acoustic sensor(s) inputs 912, power(s) inputs 913, resistance(s) inputs 914, CO2 sensor(s) inputs 915, and/or spirometer inputs 916. The control system 920 can receive inputs from the user or stored parameter values in a memory 624 (shown in FIG. 11). The control system 920 can dynamically adjust flow rate for a patient over the time of their therapy. The control system 920 can continuously detect system parameters and patient parameters. A person of ordinary skill in the art will appreciate based on the disclosure herein that any other suitable inputs and/or outputs can be used with the control system 920.

Figure 11B:
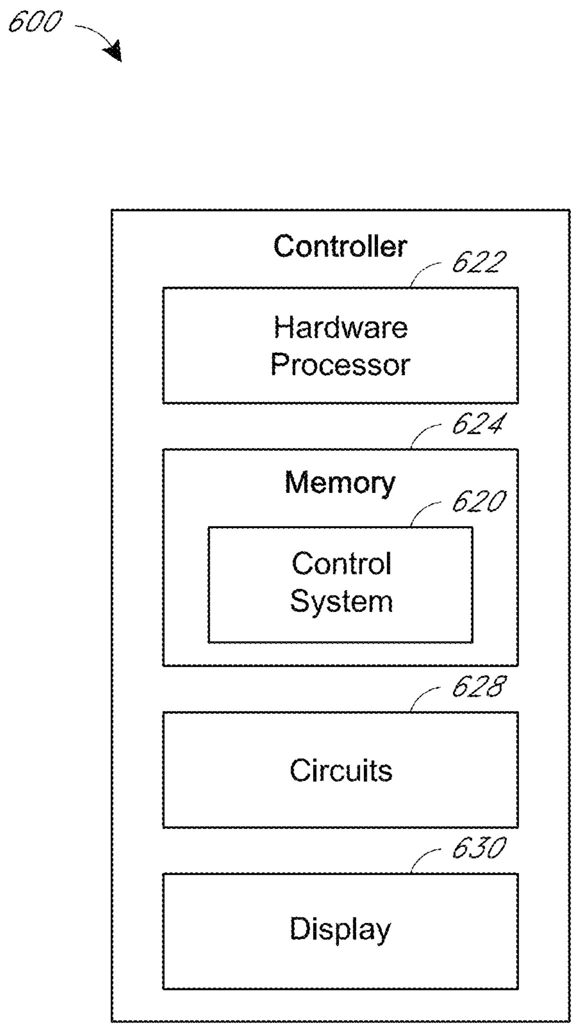
FIG. 11B illustrates a block diagram of an example controller.

FIG. 11B illustrates a block diagram of an example controller 600. The controller 600 can include programming instructions for detection of input conditions and control of output conditions. The programming instructions can be stored in the memory 624 of the controller 600. The programming instructions can correspond to the methods, processes and functions described herein. The programming instructions can be executed by one or more hardware processors 622 of the controller 600. The programming instructions can be implemented in C, C++, JAVA, or any other suitable programming languages. Some or all of the portions of the programming instructions can be implemented in application specific circuitry 628 such as ASICs and FPGAs.

The controller 600 can also include circuits 628 for receiving sensor signals. The controller 600 can further include a display 630 for transmitting status of the patient and the respiratory assistance system. The display 630 can also show warnings and/or other alerts. The display 630 can be configured to display characteristics of sensed gas(es) in real time or otherwise. The controller 600 can also receive user inputs via the user interface such as the display 630. The user interface can include button(s) and/or dial(s). The user interface can comprise a touch screen.

Figure 12:
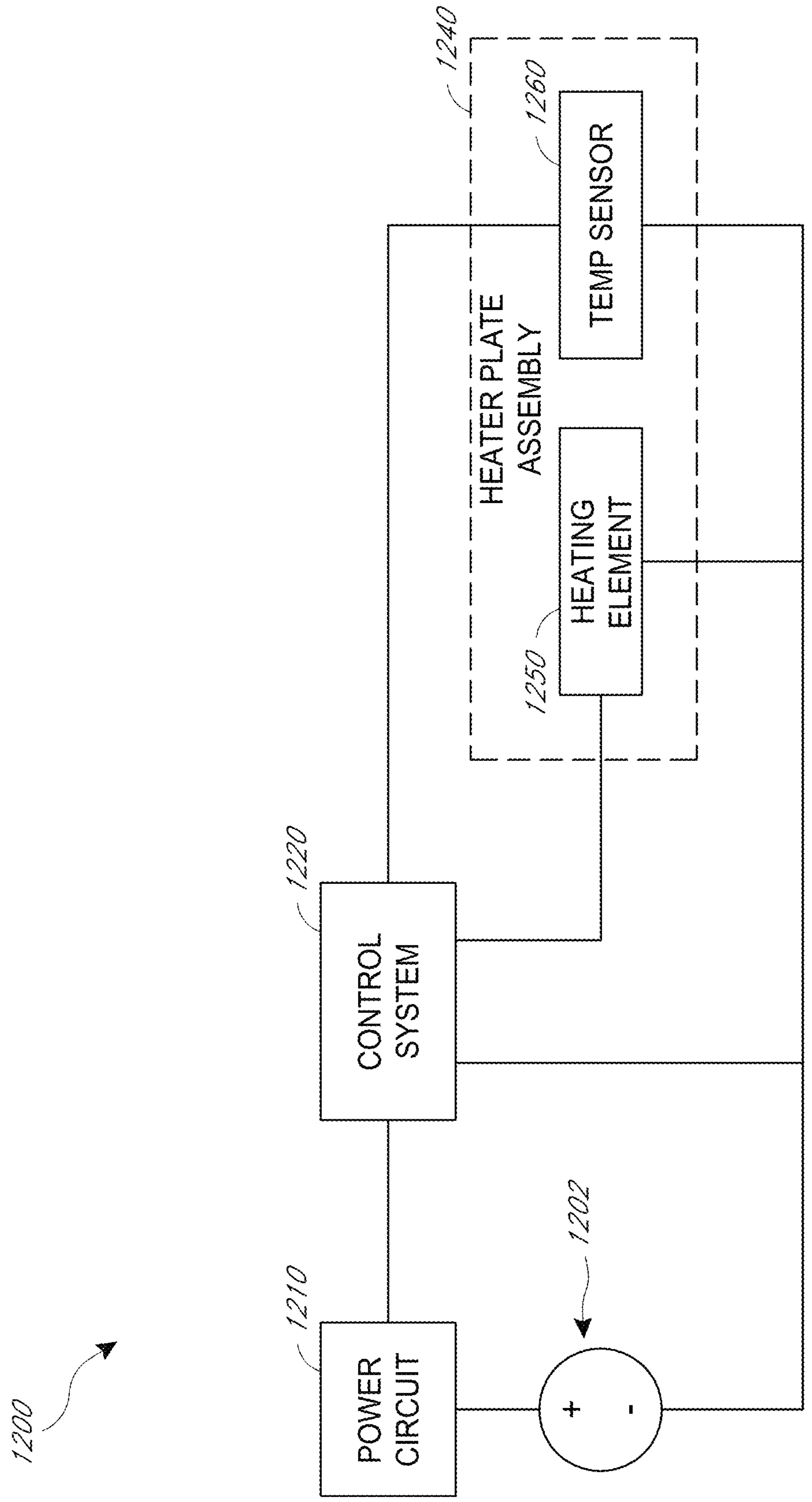
FIG. 12 illustrates an example schematic block diagram of an example system for controlling a heater plate assembly.

FIG. 12 illustrates an example schematic block diagram of an example circuit 1200 for controlling a heater plate assembly. The circuit 1200 can be implemented as part of the control system described above. The circuit 1200 can include a power source 1202 in communication with the power circuit 1210. The control system 1220 is in communication with the power circuit 1210. The control system 1220 is also in communication with a heating element 1250 and a temperature sensor 1260 (or more than one temperature sensor) of a heater plate 1240. The heating element 1250, the temperature sensor 1260, and the heating plate 1240 are examples of the same components discussed above.

The power source 1202 can be an AC or DC power source. For instance, the device incorporating the circuit 1200 can connect to an AC mains power source 1202 or can have a battery power source 1202. The power source 1202 can operate at a low voltage. For instance, the voltage may be in the range of about 20 V to a 60 V, about 30 V to about 50 V, about 35 V to about 40 V, or about 38 V. A lower voltage system can be safer for users, who are less likely to be exposed to high voltages. Further, with lower voltages, it can be simpler to make the system portable as it can run on a battery. The power circuit 1210 can include an AC/DC converter to convert AC mains voltage to DC voltage. The power circuit 1210 can also include a voltage regulator to establish an approximately set DC voltage output.

IV. Additional Examples

The heating element can be overmolded. The overmold can provide electrical insulation between the heating plate and the heating element. The overmold can be a silicone overmold. This has the added benefit of sealing the region below the heating element. However, this overmolding may also be omitted because any water that works its way below the heater plate assembly may simply drain out the bottom of the main housing, making the sealing function less necessary.

A paste that does not function as an adhesive could be used in place of the intermediate layer 570 to provide an even surface for heat transfer. This would then be paired with mechanical features, such as clips, to hold the heating element in place against the heating plate.

V. Terminology

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as “can,” “could,” “might,” or “may,” unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms “approximately,” “about,” “generally,” and “substantially” as used herein represent a value, amount, or characteristic close to the stated value, amount, or characteristic that still performs a desired function or achieves a desired result. For example, the terms “approximately”, “about”, “generally,” and “substantially” may refer to an amount that is within less than 10% of, within less than 5% of, within less than 1% of, within less than 0.1% of, and within less than 0.01% of the stated amount.

The scope of the present disclosure is not intended to be limited by the specific disclosures of embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A respiratory humidification system configured to humidify a flow of respiratory gases supplied to a user, the respiratory humidification system comprising:

a main housing configured to receive a removable humidification chamber;

a heating plate configured to be included in the main housing and positioned to contact the removable humidification chamber and transfer heat to the removable humidification chamber;

a heating element configured to provide heat to the heating plate, the heating element comprising a substrate, the heating element further comprising a resistive track or resistive pads on the substrate;

a plurality of temperature sensors disposed proximate one another and in or adjacent a center of the substrate and spaced from the resistive track or the resistive pads;

wherein a spacing between the plurality of temperature sensors and the resistive track or the resistive pads is greater than a spacing between portions of the resistive track or the resistive pads; and wherein the resistive track or the resistive pads extend around the center of the substrate and is/are not disposed in the center of the substrate.

2. The respiratory humidification system of claim 1, wherein the respiratory humidification system is configured to reduce a likelihood of the resistive track or the resistive pads causing an incorrect measurement by the plurality of temperature sensors by disposing the plurality of temperature sensors in the center of the substrate and spaced from the resistive track or the resistive pads.

3. The respiratory humidification system of claim 1, wherein the spacing between the plurality of temperature sensors and the resistive track or the resistive pads is 1 cm to 20 cm, or 2 cm to 15 cm, or 5 cm to 10 cm, or 6 cm to 7 cm.

4. The respiratory humidification system of claim 1, wherein the resistive track or the resistive pads is/are wound in turns on the substrate.

5. The respiratory humidification system of claim 1, wherein the plurality of temperature sensors connect with conductors that terminate proximate an end of the substrate.

6. The respiratory humidification system of claim 5, further comprising a flexible PCB connected to the conductors.

7. The respiratory humidification system of claim 6, wherein the flexible PCB is connected to the conductors and the resistive track or the resistive pads.

8. The respiratory humidification system of claim 1, further comprising a shroud between the heating element and the heating plate and a recessed region of the main housing sized and shaped to receive the heating element and allow the heating element to sit within the recessed region.

9. A respiratory humidification system configured to humidify a flow of respiratory gases supplied to a user, the respiratory humidification system comprising:

a main housing configured to receive a removable humidification chamber;

a heating plate configured to be included in the main housing and positioned to contact the removable humidification chamber and transfer heat to the removable humidification chamber;

a heating element configured to provide heat to the heating plate, the heating element comprising a substrate, the heating element further comprising a resistive track or resistive pads on the substrate;

a plurality of temperature sensors, wherein the resistive track or the resistive pads is/are arranged to define a central region of the substrate, the plurality of temperature sensors disposed proximate one another and are closer to a center of the substrate than an outer perimeter of the substrate and spaced from the resistive track or the resistive pads;

wherein a spacing between the plurality of temperature sensors and the resistive track or the resistive pads is greater than a spacing between portions of the resistive track or the resistive pads; and wherein the resistive track or the resistive pads extend around the center of the substrate and is/are not disposed in the central region of the substrate.

10. The respiratory humidification system of claim 9, wherein the respiratory humidification system is configured to reduce a likelihood of the resistive track or the resistive pads causing an incorrect measurement by the plurality of temperature sensors by disposing the plurality of temperature sensors in the central region and spaced from the resistive track or the resistive pads.

11. The respiratory humidification system of claim 9, wherein the spacing between the plurality of temperature sensors and the resistive track or the resistive pads is 1 cm to 20 cm, or 2 cm to 15 cm, or 5 cm to 10 cm, or 6 cm to 7 cm.

12. The respiratory humidification system of claim 9, wherein the resistive track or the resistive pads is/are wound in turns on the substrate.

13. The respiratory humidification system of claim 9, wherein the plurality of temperature sensors connects with conductors that terminate proximate an end of the substrate.

14. The respiratory humidification system of claim 13, further comprising a flexible PCB connected to the conductors and the resistive track or the resistive pads.

15. The respiratory humidification system of claim 9, further comprising a shroud between the heating element and the heating plate and a recessed region of the main housing sized and shaped to receive the heating element and allow the heating element to sit within the recessed region.

* * * * *